(12) United States Patent
Warren et al.

(10) Patent No.: US 6,213,409 B1
(45) Date of Patent: Apr. 10, 2001

(54) TIME RELEASE FRAGRANCE SACHET, METHOD OF USING SAME AND METHOD OF FABRICATING SAME

(75) Inventors: Craig B. Warren, Long Branch, NJ (US); John Ramsbotham, Hoevelaken (NL); Marcel Belt, Milan (IT)

(73) Assignees: International Flavors & Fragances Inc., New York, NY (US); Unilever Patent Holdings B.V., Vlaardingen (NL)

( * ) Notice: Subject to any disclaimer, the term of this patent is extended or adjusted under 35 U.S.C. 154(b) by 0 days.

(21) Appl. No.: 09/252,016

(22) Filed: Feb. 18, 1999

Related U.S. Application Data
(60) Provisional application No. 60/078,562, filed on Mar. 19, 1998.

(51) Int. Cl.[7] ....................................................... A61L 9/04
(52) U.S. Cl. .................... 239/53; 239/34; 239/54; 239/55; 239/60; 428/35.2; 428/36.4; 424/401
(58) Field of Search .................................. 239/34, 53, 54, 239/55, 56, 57, 58, 59, 60; 428/35.2, 35.5, 35.7, 36.4; 424/401

(56) References Cited

U.S. PATENT DOCUMENTS

| | | |
|---|---|---|
| 4,469,613 * | 9/1984 | Munteanu et al. ..................... 252/92 |
| 4,521,541 * | 6/1985 | Rutherford et al. .................... 521/79 |
| 4,605,165 | 8/1986 | Van Loveren et al. . |
| 4,854,501 | 8/1989 | Ricci ........................................ 239/54 |
| 5,849,310 * | 12/1998 | Trinh et al. ........................... 424/401 |

FOREIGN PATENT DOCUMENTS

| | | |
|---|---|---|
| 0081791 | 12/1982 | (EP) ................................. A61L/9/12 |
| 8500981 | 3/1985 | (WO) . |
| 8801515 | 3/1988 | (WO) . |
| 9732474 | 9/1997 | (WO) . |

* cited by examiner

*Primary Examiner*—Andres Kashnikow
*Assistant Examiner*—Robin O. Evans

(57) ABSTRACT

Described is a time release fragrance sachet for air freshening, particularly for use in clothing storage cabinets. The sachets comprise a container fabricated from a substance either sufficiently porous for perfumes to pass therethrough or having openings capable of permitting fragrances to pass through the walls thereof. The sachets each contain thermoplastic particles which have contained in the interstices thereof fragrance materials. The polymer particles can be foamed particles produced using chemical blowing agents or direct gas extrusion processes. Also described are methods for fabricating such sachets and methods of using same.

7 Claims, 21 Drawing Sheets

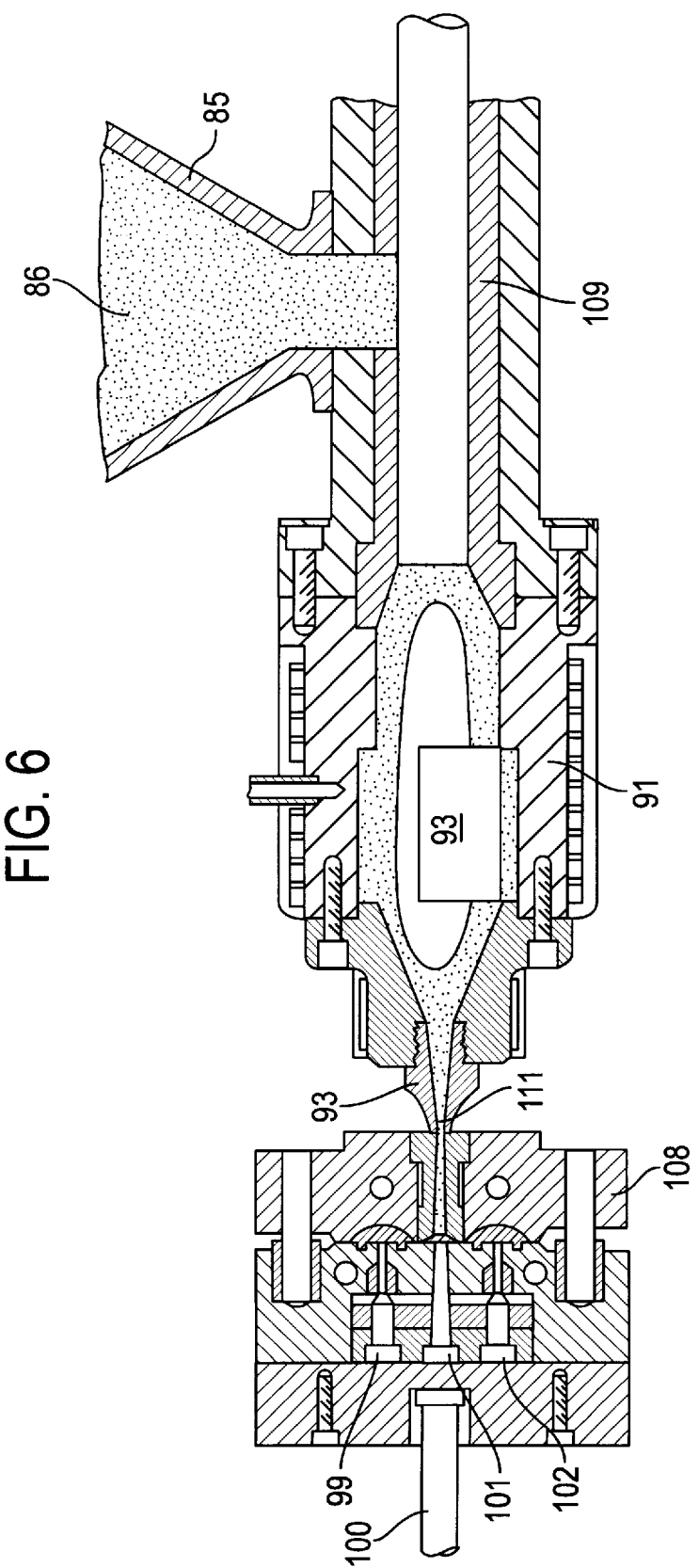

FIG. 13

7g V10 = 100% PERFUMED VERMICULITE (10% PERFUME)

3g V10 + 3.5G P10 = MIX: 50% PERFUMED VERMICULITE (10% PERFUME AND 50% POLYIFF (10% PERFUME)

3.5g VO + 3.5g P20 = MIX: 50% UNPERFUMED VERMICULITE AND 50% POLYIFF (20% PERFUME)

7g P10 = 100% POLYIFF (10% PERFUME)

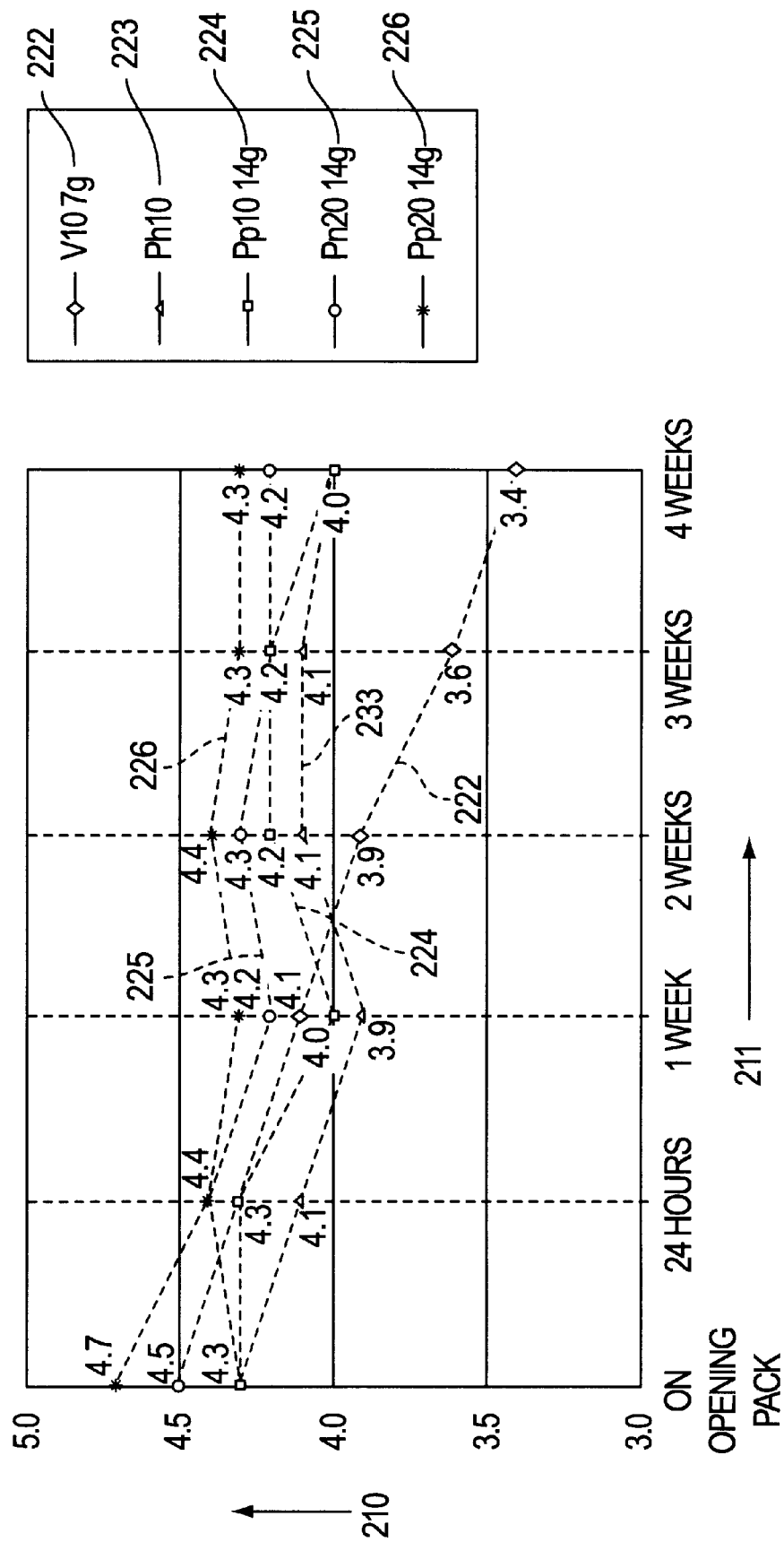

FIG. 14

0 = NO PERFUME

1 = SLIGHT PERFUME

2 = MODERATE PERFUME

3 = STRONG PERFUME

4 = VERY STRONG PERFUME

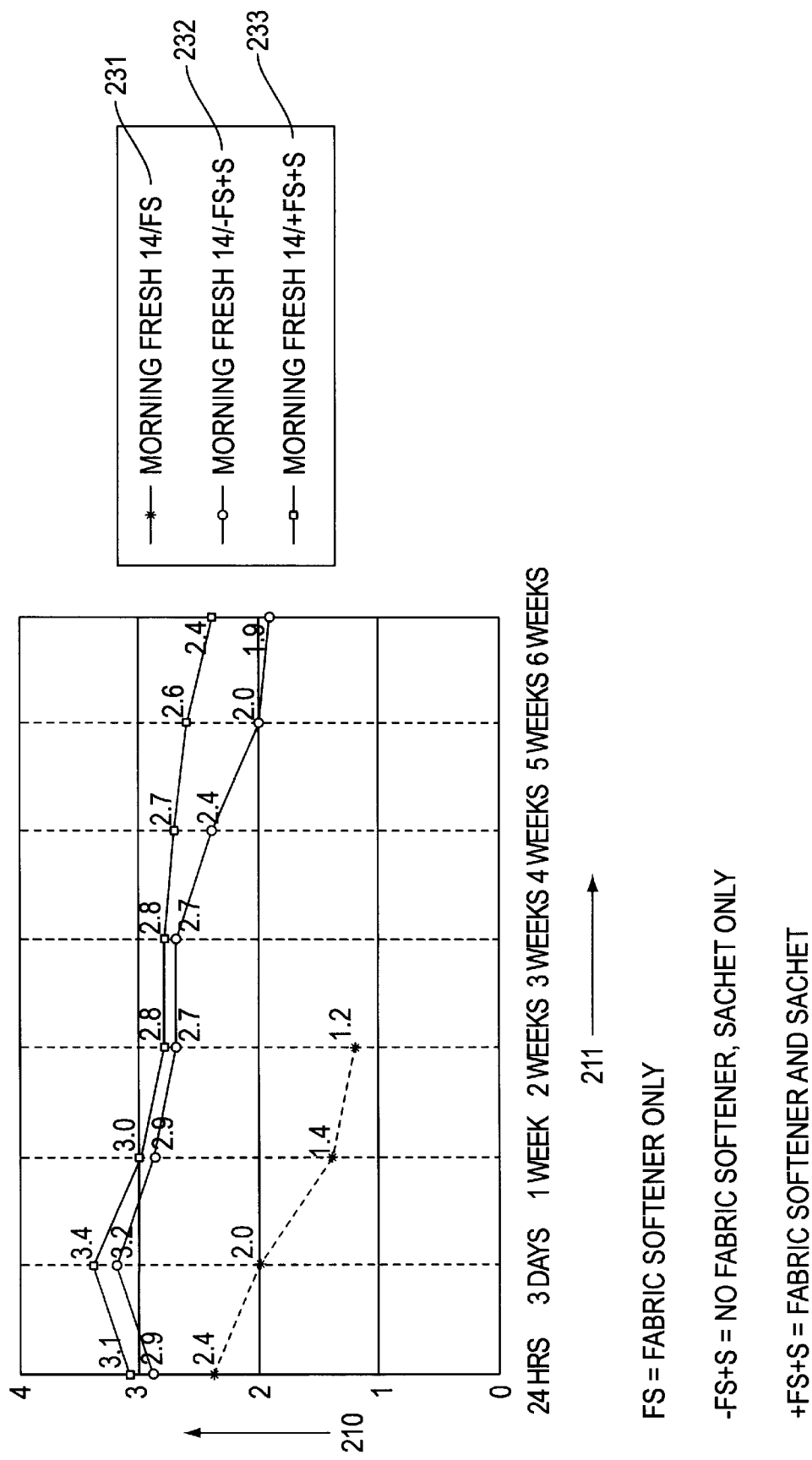

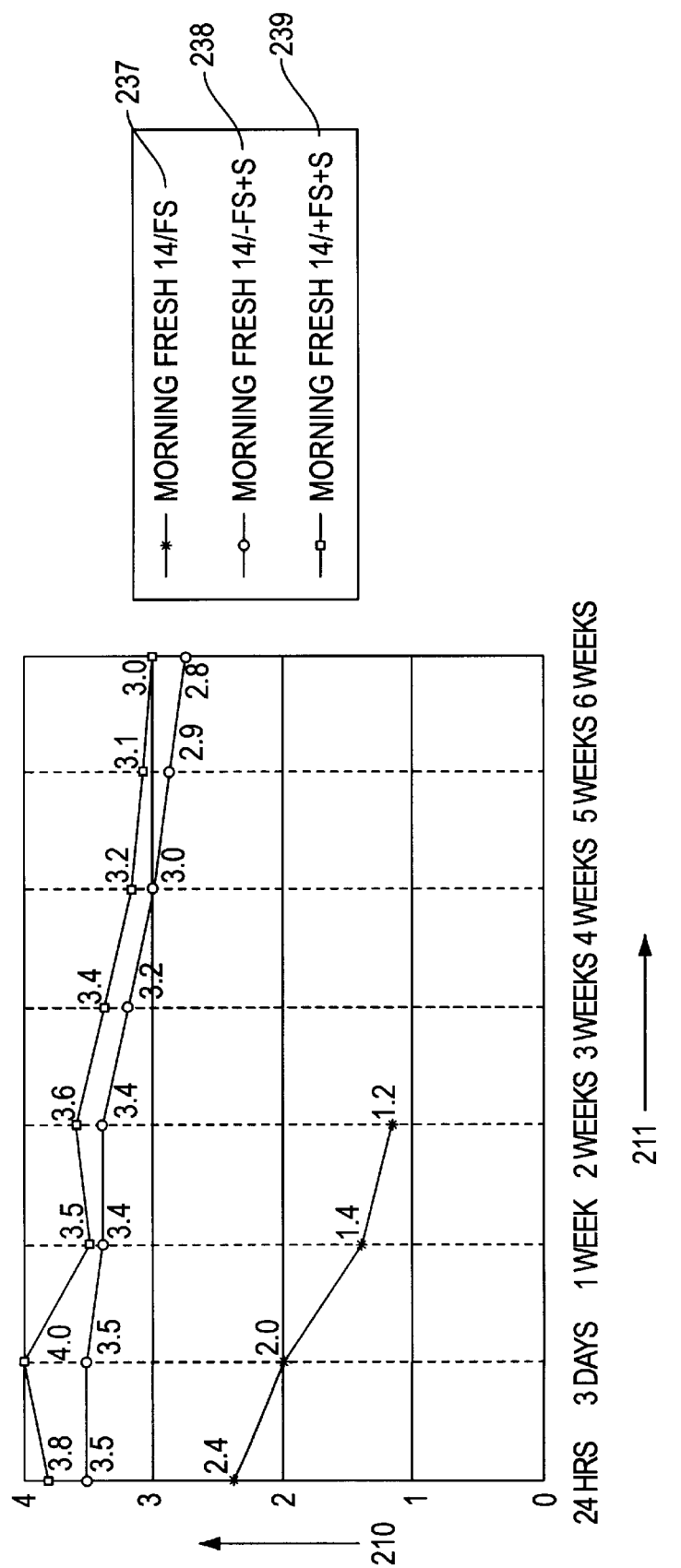

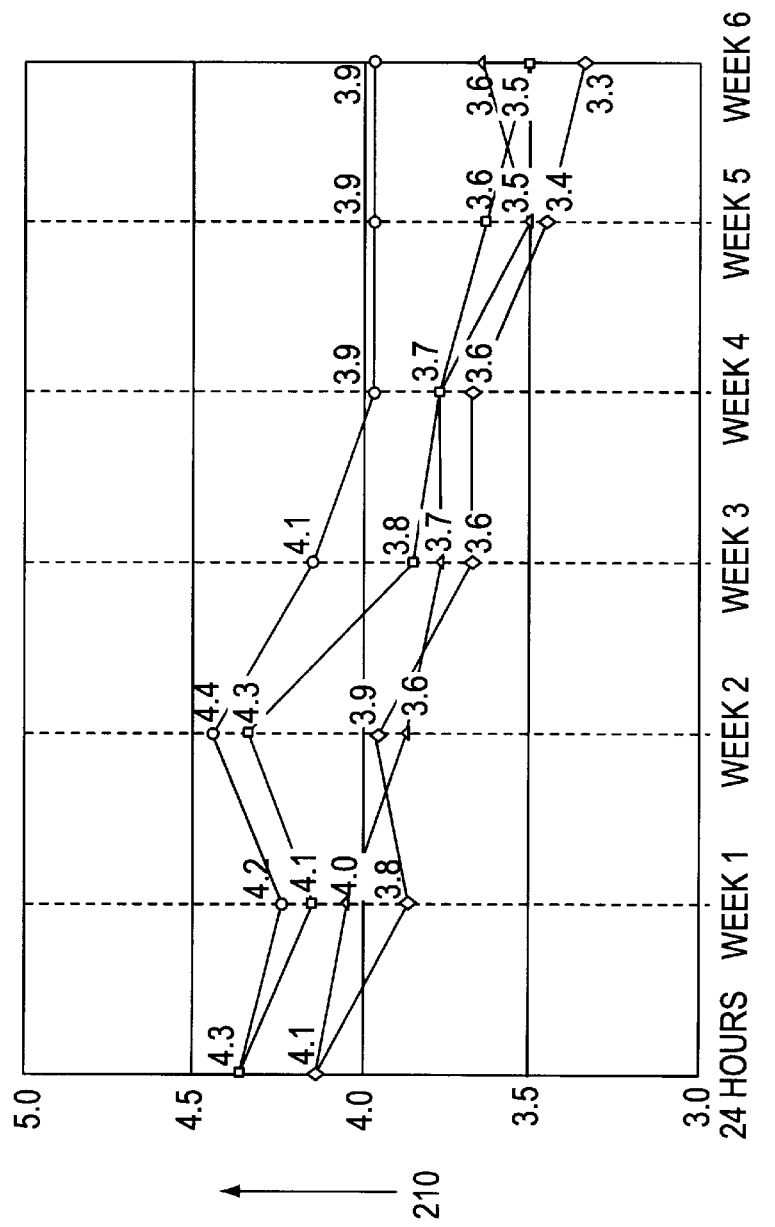

FIG. 15

5 = VERY STRONG

4 = STRONG

3 = FAIR

2 = WEAK

1 = VERY WEAK

TIME RELEASE FRAGRANCE SACHET, METHOD OF USING SAME AND METHOD OF FABRICATING SAME

RELATED CO-PENDING PATENT APPLICATIONS

This application is a Continuation-in-Part of Provisional Specification, Ser. No. 60/078,562 filed on Mar. 19, 1998 and entitled "TIME RELEASE FRAGRANCE SACHET, METHOD OF USING SAME AND METHOD OF FABRICATING SAME." Benefit of said specification, Ser. No. 60/078,562 is hereby claimed under 35 U.S.C. §119(e).

BACKGROUND OF THE INVENTION

This invention relates to time release fragrance sachets, methods of using same and methods of fabricating same. The sachets contain thermoplastic polymeric particles, including polymeric foam particles as control release compositions for use in the sachets.

An ever increasing requirement for air fresheners, including air fresheners for stored clothing exists for a slow controlled release device for slowly and controllably releasing fragrances into a gaseous environment in order to freshen air and in order to prevent stored clothing from becoming mildewed.

Slow release polymers containing perfumes are well known in the prior art. Thus, United Kingdom Patent Specification No. 1,589,201 assigned to Hercules, Inc. discloses a thermoplastic resin body consisting of a thermoplastic polymer of ethylene and 6–60 weight percent of a polar vinyl monomer selected from the group consisting of vinyl acetate, methyl acrylate, ethyl acrylate, butyl acrylate and acrylic acid wherein the perfumed resin body is suitable for the preparation of shaped objects from which perfume odor emanates over a prolonged period at a stable level U.S. Pat. No. 3,505,432 discloses a method of scenting a polyolefin which comprises:

(a) mixing a first amount of liquid polyolefin, e.g., polyethylene or polypropylene with a relatively large amount of scent-imparting material to form a flowable mass;

(b) forming drops from said mass and causing substantially instantaneous solidification of said drops into polyolefin pellets having a relatively large amount of scent-imparting material imprisoned therein;

(c) melting said pellets with a second amount of said polyolefin, said second amount being larger than said first amount; and (d) solidifying the melt of (c).

U.S. Pat. No. 4,247,498 issued on Jan. 27, 1981 discloses microporous polymers which are capable of containing volatile substances such as perfumes and the like in forms ranging from films to blocks in intricate shapes from synthetic thermoplastic polymers such as olefinic, condensation or oxidation polymers. In one embodiment of U.S. Pat. No. 4,247,498, the microporous polymers are characterized by relatively homogeneous three-dimensional cellular structure having cells connected by pores of smaller dimension. Also disclosed in U.S. Pat. No. 4,247,498 is a process for making microporous polymers from such thermoplastic polymers by heating a mixture of the polymer and compatible liquid (e.g., a perfume substance or the like) to form a homogeneous solution, cooling said solution under non-equilibrium thermodynamic conditions to initiate liquid-liquid phase separation and continuing said cooling until the mixture achieves substantial handling strength. Also disclosed in said U.S. Pat. No. 4,247,498 are microporous polymer products which contain relatively large amounts of such functionally useful fluids as perfume compositions and behave as solids.

U.S. Pat. No. 4,156,067 issued on May 22, 1979 discloses polyurethane polymers characterized by a molecular weight of above 6,000 and having lactone groups and hydroxyl groups in the polymer backbone being prepared by reacting a mixture of polyols, a polyfunctional lactone (e.g., epsilon caprolactone) and a polyfunctional isocyanate proportioned so as to provide certain desired polymer properties. It is indicated in said U.S. Pat. No. 4,156,067 that the product is soluble in alkaline solutions and may be used for light sensitive photographic layers on films, paper or glass; in drug delivery systems, as burn dressings; in body implants such as vascular prosthesis; in molding compositions; and in the manufacture of catheters as well as in delivery of perfume compositions in a slow release manner. It is further indicated in said U.S. Pat. No. 4,156,067 that the water absorptivity of the polyurethane/lactone polymers is above 10%, preferably in the range of about 20% to 60%, and these polymers may range in their physical properties from rigid solids to completely gel-like high water absorptive polymers. It is further indicated in said U.S. Pat. No. 4,156,067 that the polymers provide a leachable substrate wherein the leaching agent may be water, gases, alcohols, esters and body fluids, e.g., animal or human.

Extrusion of thermoplastic foams is well known in the prior art. Thus, the *Modern Plastics Encyclopedia* (published by the McGraw-Hill Publishing Company), 1982–1983 edition at pages 274 and 275 discloses a section authored by Fred Schrafft entitled "Extruding Thermoplastic Foams." Said article on pages 274 and 275 is incorporated by reference herein. It is indicated therein that three different processes are used for the extrusion of thermoplastic foams:

(i) extrusion of expandable beads;

(ii) extrusion of thermoplastics containing a chemical blowing agent; and (iii) direct gas extrusion process.

It is further indicated in the Schrafft article that the extrusion using a chemical blowing agent may be carried out on a normal single screw extruder, and the direct gas extrusion process may be carried out on single and twin screw extruders. It is further indicated in the Schrafft article that common blowing agents used in the process are hydrocarbons such as pentene or fluorocarbons such as 11, 12 and 114. It is further stated that:

"the amount of blowing agent can vary widely depending on the resin and the type of product desired. However, generally about 7% blowing agent produces a product of about 5.6 lbs/cu. ft., while 18% blowing agent produces a product of about 1.9 lbs/cu. ft. . . . "

BRIEF DESCRIPTION OF THE DRAWINGS

FIG. 5A shows the apparatus immediately prior to the carrying out of the injection molding process and FIG. 5B shows the apparatus during the injection molding process wherein the polymeric foamed pellets are being fused and pushed through the injection molding apparatus orifice into the mold.

FIG. 6 is a cutaway side elevation view of injection molding apparatus useful in forming articles from the polymeric pellets containing fragrance useful in practicing our invention.

FIG. 12A shows one part of the preformed sachet containing fragrance-containing polymeric particles ready to be heat sealed to the second part of the sachet to form the sachet of FIG. 11.

FIG. 12B shows the other part of the sachet prior to forming, ready to be heat sealed to that part of the sachet as illustrated in FIG. 12A.

FIG. 13 sets forth a diagram indicating the symbols used in the drawings of FIGS. 13A, 13B, 13C and 13D.

FIGS. 13B, 13C and 13D show graphs similar to those of FIG. 13A with different concentrations of fragrance and different amounts of perfumed polymer located within each sachet.

FIG. 14 is a diagram setting forth the scale used for FIGS. 14A, 14B, 14C, 14D and 14E.

FIGS. 14A, 14B, 14C, 14D and 14E set forth in-use graphs for sachets containing the products as set forth in FIG. 14 with strength on a scale of zero to 5 on the Y axis and time being set forth on the X axis of each graph.

FIG. 15 sets forth another scale used for the graphs of FIGS. 13A, 13B, 13C, 13D, 14A, 14B, 14C, 14D and 14E.

In summary, the graphs of FIGS. 13A, 13B, 13C and 13D show the performance of mixtures of perfumed polymer and vermiculite (expanded clay) with different perfume loadings (10% and 20%) and different weights of particles (7 grams and 14 grams). The graphs of FIGS. 14A, 14B, 14C and 14D show sachet performance with and without liquid fabric softener. The graph of FIG. 14E shows lavender sachet performance at different weights and perfume loadings.

Figure 16:
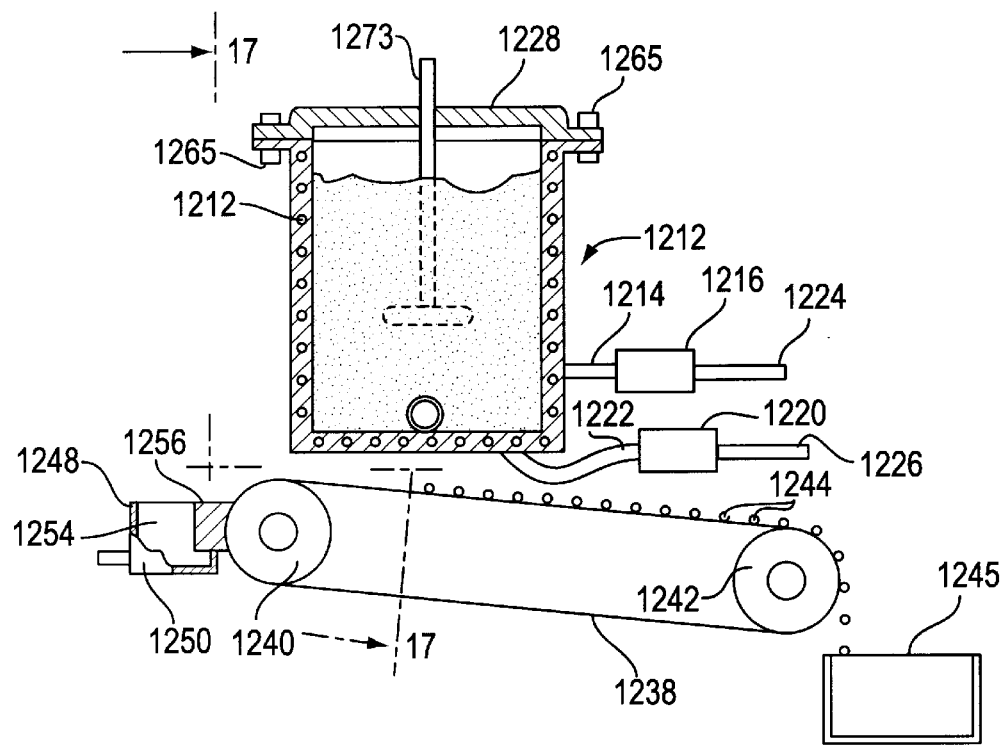

FIG. 16 is a partial side elevation view and partial sectional view of an apparatus for forming non-foamed polymer pellets containing fragrances useful in the practice of our invention.

Figure 17:
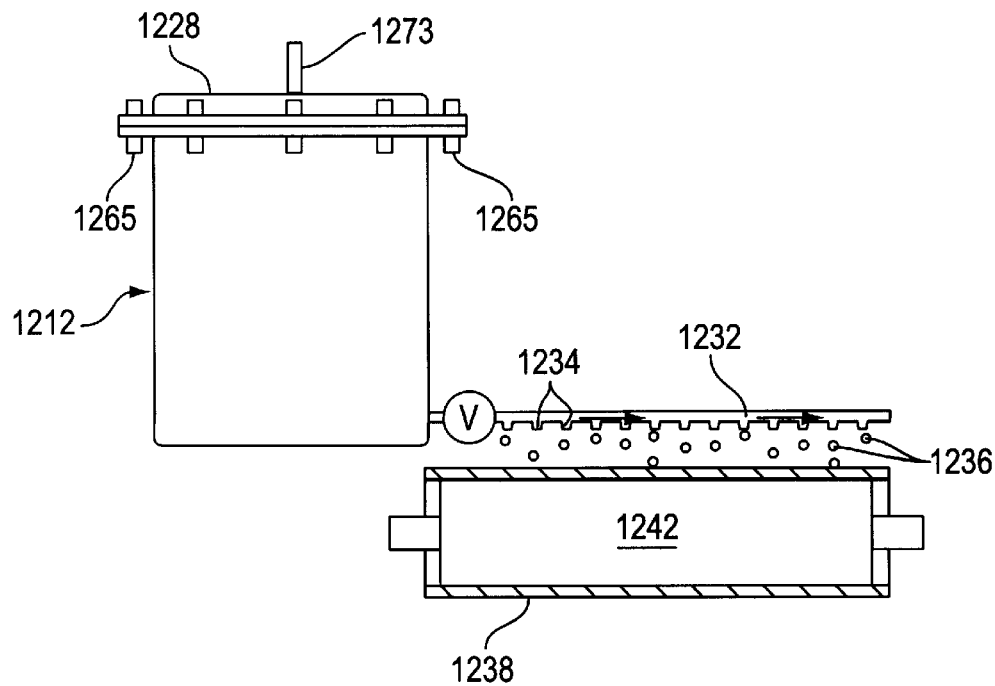

FIG. 17 is a section taken along line 17—17 of FIG. 16,

SUMMARY OF THE INVENTION

Our invention concerns time release fragrance sachets, methods of using same and methods of fabricating same.

The time release sachets of our invention comprise hollow container means fabricated from porous or non-porous materials. The porous materials are porous to the fragrances contained within perfumed polymer particles located within the sachet.

The perfumed particles are fabricated using extrusion techniques and according to techniques as set forth in U.S. Pat. No. 4,521,541 issued on Jun. 4, 1985, the specification for which is incorporated by reference herein; U.S. Pat. No. 4,542,162 issued on Sep. 17, 1985, the specification for which is incorporated by reference herein; as well as U.S. Pat. No. 5,543,398 issued on Aug. 6, 1996, the specification for which is incorporated by reference herein.

The polymer particles, containing the perfumes located within the sachet, contain perfumes as defined in U.S. Pat. No. 5,540,853 issued on Jul. 30, 1996, the specification for which is incorporated by reference herein.

Preferably, the perfume particles useful in the practice of our invention are "puffed" as a result, of gaseous entrainment, which is carried out during the formation of said particles by means of extrusion.

Preferably, the sachets of our invention are fabricated from perfume-porous materials with heat sealed closures. However, the enclosures of our invention may be fabricated from non-porous materials if the walls have discrete openings so that fragrances may pass therethrough as they are being emitted from the control release fragrance-containing polymeric particles.

Examples of perfume-porous materials are synthetics nonwoven polyesters, synthetic nonwoven polypropylene and natural woven cotton interlock materials. The sachet enclosures are fabricated from substances having from about 30 up to about 120 grams per square centimeter (gsm) as a measurement of the weave. The geometry of the sachets of our invention may be spherical, ellipsoidal, cylindrical or conical. The dimensions may be such that the height may vary from about 3 inches up to about 6 inches; the width may vary from about 2 inches up to about 5 inches; and, in the case of a spherical sachet, the diameter may vary from about 3 inches up to about 5 inches.

The perfumed polymer particle weight within each sachet may vary from about 2 grams up to about 14 grams, with a preferred range of from about 3 grams up to about 5 grams of perfumed particle. The size of each perfumed particle may vary from about 0.05 cm up to about 1 cm and preferably a diameter of from about 3 up to about 7 mm.

The fragrance material within the polymer has a calculated $\log_{10} P$ in the range of from about 3 up to about 8, wherein P is the partition coefficient of the active or bioactive material between n-octanol and water.

The perfume ingredients are preferred to have a boiling point $\geq 250°$ C. The logP of many perfume ingredients has been reported; for example, the Pomona92 database, available from Daylight Chemical Information Systems, Inc. (Daylight CIS), Irvine, Calif., contains many, along with citations to the original literature. However the logP values are most conveniently calculated by the "CLOGP" program, also available from Daylight CIS. This program also lists experimental logP values when they are available in the Pomona92 database. The "calculated logP" (ClogP) is determined by the fragment approach of Hansch and Leo (cf., A. Leo, in *Comprehensive Medicinal Chemistry*, Volume 4, C. Hansch, P. G. Sammens, J. B. Taylor and C. A. Ramsden, editors, page 295, Pergamon Press, 1990, incorporated by reference herein). The fragment approach is based on the chemical structure of each perfume ingredient and takes into account the numbers and types of atoms, the atom connectivity and the chemical bonding. The ClogP values, which are the most reliable and widely used estimates for this physiochemical property, are preferably used instead of the experimental logP values in the selection of perfume ingredients which are useful in the present invention.

Non-enduring perfume ingredients, which are preferably minimized in personal treatment, e.g., liquid personal cleansing compositions of the present invention, are those having a B.P. of less than about 250° C. or having a ClogP of less than about 3.0 or having both a B.P. of less than about 250° C. and a ClogP of less than about 3.0. The table below gives some non-limiting examples of non-enduring perfume ingredients. In some particular fabric softener compositions, some non-enduring perfume ingredients can be used in small amounts, e.g., to improve product odor. However, to minimize waste, the enduring perfume compositions of the present invention contain less than about 30 weight percent of non-enduring perfume ingredients, preferably less than about 25 weight percent of non-enduring perfume ingredients, more preferably, less than about 20 weight percent of non-enduring perfume ingredients, and even more preferably, less than about 15 weight percent of non-enduring perfume ingredients Examples of perfume materials which have a calculated logP$\geq$3 are as set forth in the following table:

Examples of Enduring Perfume Ingredients

| Perfume Ingredients | Approximate B.P. (° C.)[a] | ClogP |
|---|---|---|
| B.P. > 250° C. and ClogP > 3.0 | | |
| Allyl cyclohexane propionate | 267 | 3.935 |
| Ambrettolide | 300 | 6.261 |
| Amyl benzoate | 262 | 3.417 |
| Amyl cinnamate | 310 | 3.771 |
| Amyl cinnamic aldehyde | 285 | 4.324 |
| Amyl cinnamic aldehyde dimethyl acetal | 300 | 4.033 |
| iso-Amyl salicylate | 277 | 4.601 |
| Aurantiol | 450 | 4.216 |
| Benzophenone | 306 | 3.120 |
| Benzyl salicylate | 300 | 4.383 |
| para-tert-Butyl cyclohexyl acetate | +250 | 4.019 |
| iso-Butyl quinoline | 252 | 4.193 |
| β-Caryophyllene | 256 | 6.333 |
| Cadinene | 275 | 7.346 |
| Cedrol | 291 | 4.530 |
| Cedryl acetate | 303 | 5.436 |
| Cedryl formate | +250 | 5.070 |
| Cinnamyl cinnamate | 370 | 5.480 |
| Cyclohexyl salicylate | 304 | 5.265 |
| Cyclamen aldehyde | 270 | 3.680 |

-continued
Examples of Enduring Perfume Ingredients

| Perfume Ingredients | Approximate B.P. (° C.)[a] | ClogP |
|---|---|---|
| Dihydro isojasmonate | +300 | 3.009 |
| Diphenyl methane | 262 | 4.059 |
| Diphenyl oxide | 252 | 4.240 |
| Dodecalactone | 258 | 4.359 |
| ISO E SUPER ® | +250 | 3.455 |
| Ethylene brassylate | 332 | 4.554 |
| Ethyl methyl phenyl glycidate | 260 | 3.165 |
| Ethyl undecylenate | 264 | 4.888 |
| Exaltolide | 280 | 5.346 |
| GALAXOLIDE ® | +250 | 5.482 |
| Geranyl anthranilate | 312 | 4.216 |
| Geranyl phenyl acetate | +250 | 5.233 |
| Hexadecanolide | 294 | 6.805 |
| Hexenyl salicylate | 271 | 4.716 |
| Hexyl cinnamic aldehyde | 305 | 5.473 |
| Hexyl salicylate | 290 | 5.260 |
| α-Irone | 250 | 3.820 |
| Lilial (p-t-bucinal) | 258 | 3.858 |
| Linalyl benzoate | 263 | 5.233 |
| 2-Methoxy naphthalene | 274 | 3.235 |
| Methyl dihydrojasmone | +300 | 4.843 |
| γ-n-Methyl ionone | 252 | 4.309 |
| Musk indanone | +250 | 5.458 |
| Musk ketone | MP = 137° C. | 3.014 |
| Musk tibetine | MP = 136° C. | 3.831 |
| Myristicin | 276 | 3.200 |
| Oxahexadecanolide-10 | +300 | 4.336 |
| Oxahexadecanolide-11 | MP = 35° C. | 4.336 |
| Patchouli alcohol | 285 | 4.530 |
| Phantolide | 288 | 5.977 |
| Phenyl ethyl benzoate | 300 | 4.058 |
| Phenyl ethyl phenyl acetate | 325 | 3.767 |
| Phenyl heptanol | 261 | 3.478 |
| Phenyl hexanol | 258 | 3.299 |
| α-Santalol | 301 | 3.800 |
| Thibetolide | 280 | 6.246 |
| δ-Undecalactone | 290 | 3.830 |
| γ-Undecalactone | 297 | 4.140 |
| Vetiveryl acetate | 285 | 4.882 |
| Yara-yara | 274 | 30235 |
| Ylangene | 250 | 6.268 |

[a]M.P. is melting point; these ingredients have a B.P. higher than 250° C.

The amount of fragrance material in the perfumed polymer particles may vary from about 5% up to about 45% by weight of the perfumed particle.

As set forth, supra, foamed or non-foamed polymeric particles may be utilized in the practice of our invention.

The advantages of using the foamed polymeric particles are multiple, to wit:

(a) improved handling;

(b) greater retention of fragrance when not in use; and (c) greater length of time during which release of fragrance from polymer is at "steady state" or "zero order."

Whether producing foamed or non-foamed polymer, the nature of the extruder utilized in the process for producing polymeric particles of our invention may be either single screw or double screw. Thus, the types of extruders that can be used are disclosed at pages 246–267 and 332–349 of the *Modern Plastics Encyclopedia*, 1982–1983 (published by the McGraw-Hill Publishing Company), the disclosure of which is incorporated by reference herein. More specifically, examples of extruders which are usable in carrying out the process for producing the polymeric particles used in our invention are as follows:

1. The Welex "Super Twinch" 3.5 inch extruder manufactured by Welex Incorporated, 850 Jolly Road, Blue Bell, Pa. 19422;

2. The Krauss-Maffei twin screw extruder manufactured by the Krauss-Maffei Corporation/Extruder Division, 3629 West 30th Street South, Wichita, Kans. 67277;

3. Modified Sterling model 4000 and 5000 series extruder manufactured by Sterling Extruder Corporation of 901 Durham Avenue, South Plainfield, N.J.;

4. The CRT ("Counter-Rotating Tangential") Twin Screw Extruder manufactured by Welding Engineers, Inc., King of Prussia, Pa. 19406;

5. The Leistritz Twin Screw Dispersion Compounder manufactured by the American Leistritz Extruder Corporation, 198 U.S. Route 206 South, Sommerville, N.J. 08876;

6. The ZSK Twin Screw Co-Rotating Extruder manufactured by the Werner & Pfleiderer Corporation, 663 East Crescent Avenue, Ramsey, N.J. 07446;

7. The Farrel Extruder manufactured by Farrel Connecticut Division, Emhart Machinery Group, Ansonia, Conn. 06401;

8. The MPC/V Baker Perkins Twin Screw Extruder manufactured by the Baker Perkins Inc. Chemical Machinery Division, Saginaw, Mich. 48601; and 9. The Berstorff single screw, twin screw or foam extrusion equipment manufactured by Berstorff Corporation, P.O. Box 240357, 8200-A Arrowridge Boulevard, Charlotte, N.C. 28224; and In producing the polymeric particles used in the sachets of our invention, various polymers may be utilized, for example: low-density polyethylene, high-density polyethylene, polypropylene, the copolymer of ethylene and vinyl acetate and polyvinyl chloride. More specifically, the polymers used in the practice of our invention may be copolymers of ethylene and a polar vinyl monomer selected from:

(a) vinyl acetate;
(b) ethyl acrylate;
(c) methyl acrylate;
(d) butyl acrylate; and
(e) acrylic acid, including the hydrolyzed copolymer of ethylene and vinyl acetate. Preferred copolymers are ethylene vinyl acetate with about 9 to 60% vinyl acetate and ethylene/ethyl acrylate with about 6 to 18% ethyl acrylate.

Resins of the type disclosed for use as copolymers are commercially available in the molding powder form. For example, ethylene vinyl acetate copolymers are marketed by the E.I. duPont de Nemours Company under the trade name "ELVAX®" and by the Arco Polymer Division under the trademark "DYLAND®" and by the Exxon Corporation of Linden, N.J. under the trademark "DEXXON®." Ethylene/ethyl acrylate copolymers are marketed by Union Carbide Corporation under the trade name "EEA RESINS®."

The polymer is added to the single screw or twin screw extruder at a feed rate in the range of from about 80 up to about 300 lbs/hour while maintaining the temperature in the screw extruder between about 160° C. and about 240° C. If the polymer or copolymer powder is added to the extruder at a reference "barrel segment," then the fragrance is added to the extruder under pressure downstream from the addition point of the polymer at 1 or more of "barrel segments" 2–9.

The fragrance added at "barrel segments" 2–9 of the single screw or twin screw extruder then has one or more of the foregoing functions. Furthermore, the fragrance added at "barrel segments" 2–9 must be previously or made to be compatible with the polymer added at "barrel segment" 1 of the single screw or twin extruder.

As stated, supra, various polymers are useful in the practice of our invention. Specific examples of polymers useful in the practice of our invention are as follows:

(a) DYLAN® brand of low density polyethylene. DYLAN is a trademark owned by the Atlantic Richfield Company of Los Angeles, Calif.;

(b) DYLITE® brand of expandable polystyrene compositions. DYLITE® is a trademark of the Atlantic Richfield Company of Los Angeles, Calif.;

(c) SUPER DYLAN® brand of high density polyethylene. SUPER DYLAN® is a trademark of the Atlantic Richfield Company of Los Angeles, Calif.;

(d) Blended polyethylene and carbon black as specifically taught in U.S. Pat. No. 4,369,267 issued on Jan. 18, 1983, the specification for which is incorporated by reference herein;

(e) Polystyrene as disclosed in U.S. Pat. No. 4,369,227 issued on Jan. 18, 1983, the specification for which is incorporated by reference herein;

(f) Polyene/α-olefin copolymers as exemplified and disclosed in U.S. Pat. No. 4,369,291, the specification for which is incorporated by reference herein;

(g) Poly-α-olefins disclosed in Canadian Patent No. 1,137,067 issued on Dec. 7, 1982, the specification for which is incorporated by reference herein;

(h) Polymeric compositions as disclosed in Canadian Patent No. 1,137,068 issued on Dec. 7, 1982, the specification for which is incorporated by reference herein;

(i) Poly-α-olefins disclosed in Canadian Patent No. 1,137,067, the specification for which is incorporated by reference herein;

(j) Polyolefins described in Canadian Patent No. 1,137,066, the specification for which is incorporated by reference herein;

(k) Polyethylene oxides as disclosed in Canadian Patent No. 1,137,065 issued on Dec. 7, 1982, the specification for which is incorporated by reference herein;

(l) Olefin polymers and copolymers as disclosed in Canadian Patent No. 1,139,737 issued on Jan. 18, 1983, the disclosure of which is incorporated by reference herein.

(m) Polyolefins disclosed in Canadian Patent No. 1,139,738 issued on Jan. 18, 1983, the specification for which is incorporated by reference herein.

(n) Clorinated PVC as disclosed in Polymer 1982.23 (7, Suppl.), 1051–6 abstracted at *CHEMICAL ABSTRACTS*, Volume 97:145570y, 1982;

(o) Polyepsilon caprolactone copolymers made by means of alcohol initiated polymerization as disclosed in *J. Polym. Sci., Polym. Chem. Ed.* 1982, 20(2), pages 319–26, abstracted at *CHEMICAL ABSTRACTS,* Volume 96:123625x, 1982;

(p) Styrene acrylonitrile copolymers as disclosed in *Diss. Abstracts, Int. B,* 1982, 42(8), 3346 and abstracted at *CHEMICAL ABSTRACTS,* Volume 96:143750n, 1982;

(q) Copolymers of epsilon caprolactone with 1,4-butane diol as disclosed at Kauch. Rezine, 1982, (2), 8–9, abstracted at *CHEMICAL ABSTRACTS,* Volume 96:143750n, 1982;

(r) Polyesters as disclosed in U.S. Pat. No. 4,326,010, the specification for which is incorporated by reference herein;

(s) Clorinated polyethylene as disclosed by Belorgey, et al, *J. Polym. Sci.,* Polym. Phys. Ed. 1982, 20(2), 191–203

(t) Plasticized polyepsilon caprolactone copolymers containing dimethyl phthalate plasticizers as set forth in Japanese Patent No. J81/147844, abstracted at *CHEMICAL ABSTRACTS,* Volume 96:69984y (1982), the specification for which is incorporated by reference herein;

(u) Maleic anhydride modified adducts of polyepsilon caprolactone polyols and ethylenically unsaturated monomer as disclosed in U.S. Pat. No. 4,137,279 issued on Jan. 30, 1979, the specification for which is incorporated by reference herein;

(v) Polyurethane polymers having lactone backbones as disclosed in U.S. Pat. No. 4,156,067 issued on May 22, 1979, the disclosure of which is incorporated by reference herein;

(w) Polyurethane polyether resins wherein the resin is obtained by reacting a polyfunctional lactone with a long chain polyalkylene diol and a urethane precursor as disclosed in U.S. Pat. No. 4,355,550 issued on Mar. 10, 1981, the disclosure of which is incorporated by reference herein; and (x) Resins having polyurethane backbones as disclosed in U.S. Pat. No. 3,975,350 issued on Aug. 17, 1976, the disclosure of which is incorporated by reference herein.

DETAILED DESCRIPTION OF THE DRAWINGS

Figure 1A:
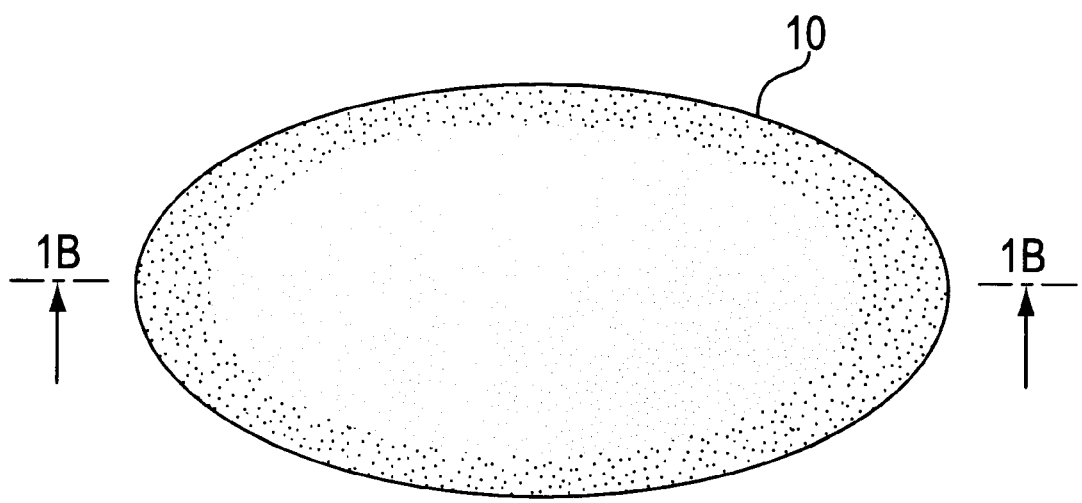
FIG. 1A represents a perspective view of the outside of a foamed polymeric particle containing fragrance produced according to the process of Example I wherein a nitrogen foaming agent and a fragrance for use in sachets were added to an extruder during the extrusion of polyethylene.

FIG. 1A is an outer view of a foamed polymeric particle containing functional fluid or solid as indicated by reference numeral 10.

Figure 1B:
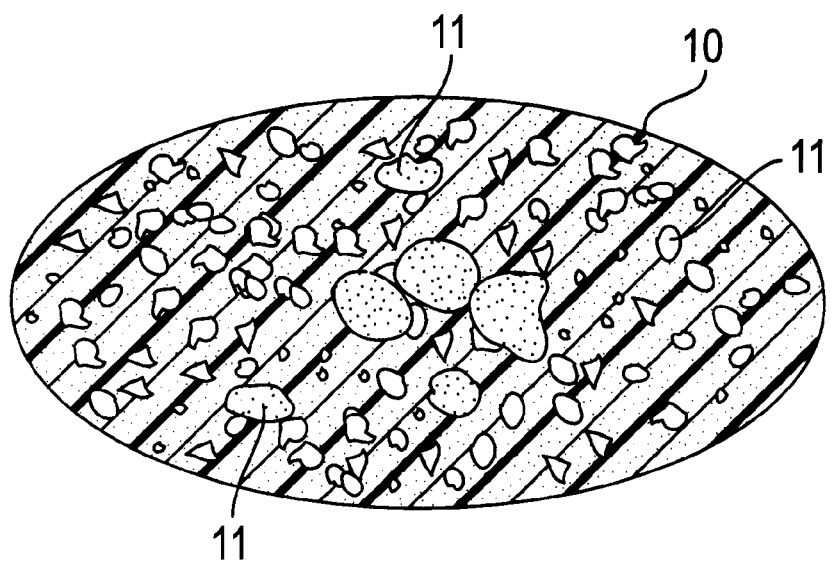
FIG. 1B is a cutaway side elevation view of the particle of FIG. 1A.

FIG. 1B is a cross-section of the particle of FIG. 1A, taken along line 1B in FIG. 1A. Part of the particle indicated by reference numeral 10 is the outer surface thereof. Reference numeral 11 indicated one of the pores produced as a result of foaming.

Figure 2:
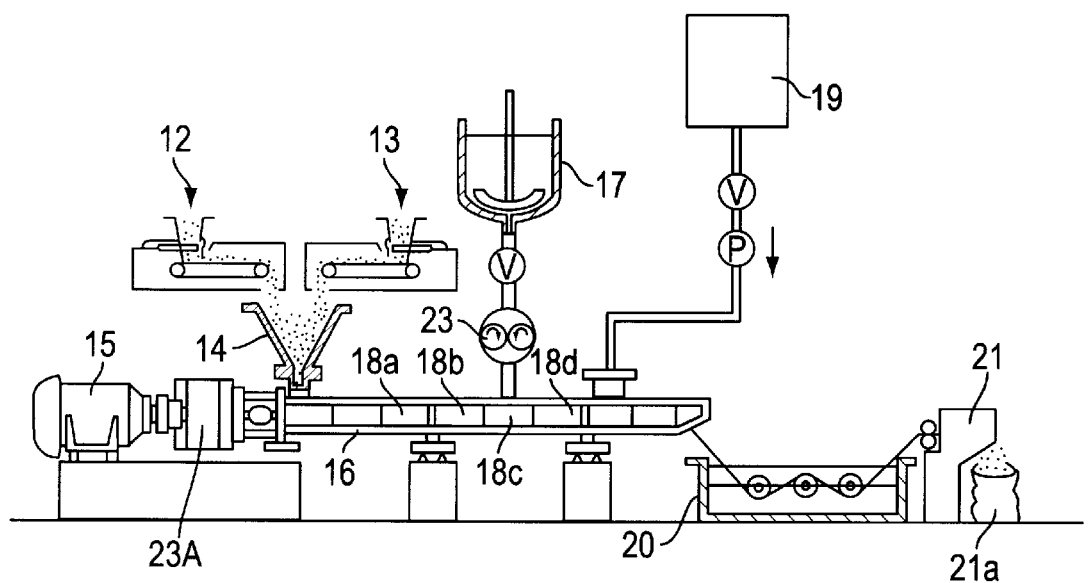
FIG. 2 is a cutaway side elevation schematic diagram of a screw extruder during the compounding of the resin with a fragrance while simultaneously adding foaming agent into the hollow portion of the barrel of the extruder and incorporates the pelletizing apparatus used in pelletizing the extruded foamed tow produced as a result of the extrusion operation.

FIG. 2 is a schematic cutaway elevation diagram of the extrusion and pelletizing apparatus useful in carrying out the process of our invention during the operation of said apparatus. Motor 15 drives the extruder screws located at 23A in barrel 16, the extruder being operated at temperatures in the range of about 150° C. up to about 250° C. At the beginning of the barrel resin at source 12 together with additives, e.g., opacifiers, processing aids, colors, pearlescent agents and densifiers at location 13 is added via addition funnel 14 into the extruder. Simultaneously (when the operation reaches "steady state"), fragrance is added to the extruder at one, two or more of barrel segments 3–8 of the extruder (which may be a twin screw or single screw extruder) at locations 18a, 18b, 18c and 18d by means of gear pump 23 from source 17. From source 19 into barrel segments 5–10, the gaseous or liquid blowing agents, e.g., nitrogen, carbon dioxide and the like as described, supra, are added simultaneously with the addition of the fragrance. The feed rate range of resin is about 80–300 lbs per hour. The feed rate range of the fragrance is between 1 and 35% of the feed rate range of the resin. The blowing agent rate range is such that the pressure of the gas or the pressure over the liquid being fed into the extruder is between about 50 and 200 psig. If desired, the extruded ribbon or cylinder may be passed through water bath 20 and pelletizer 21 into collection apparatus 21a. FIG. 22 indicates the travel of the extruded material prior to entering pelletizer 21.

Figure 3:
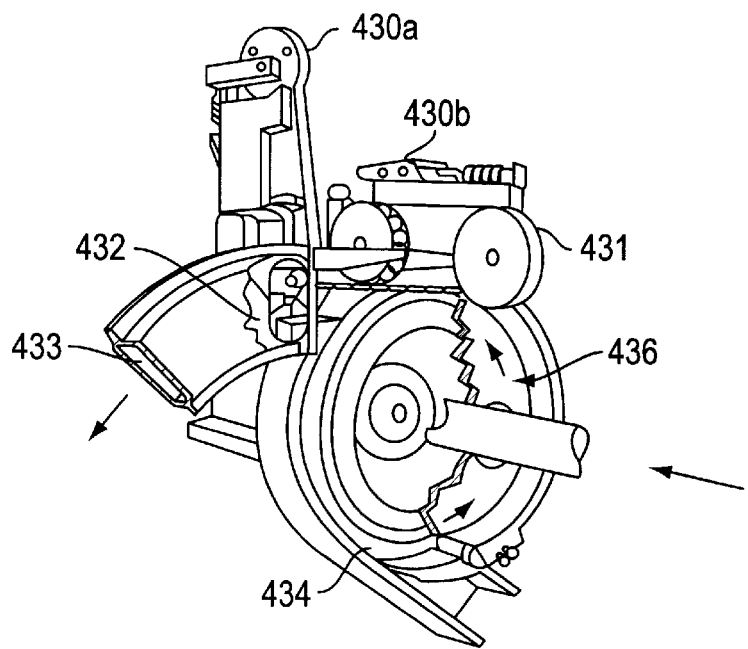
FIG. 3 is a cutaway perspective diagram of a pelletizing apparatus used in conjunction with the extrusion apparatus, for example, that illustrated in FIG. 2, whereby the extruded tow is pelletized.

FIG. 3 is a detailed cutaway perspective view of such a pelletizer as is used in conjunction with the apparatus of FIG. 2. The extruded material coming from the water cooler which is already foamed and which already contains fragrance is fed into the pelletizer at zero pressure at location 434. The pelletizer is operated using a spinning extrusion die 436 and operated by means of a rotating wheel 434. Moving pellet knife 431 and dual knife units 430a and 430b cause pellets to be formed which fly into a cooling water stream 432. The resulting pellets which are foamed and contain fragrance exit from the pelletizer at 433.

Figure 4:
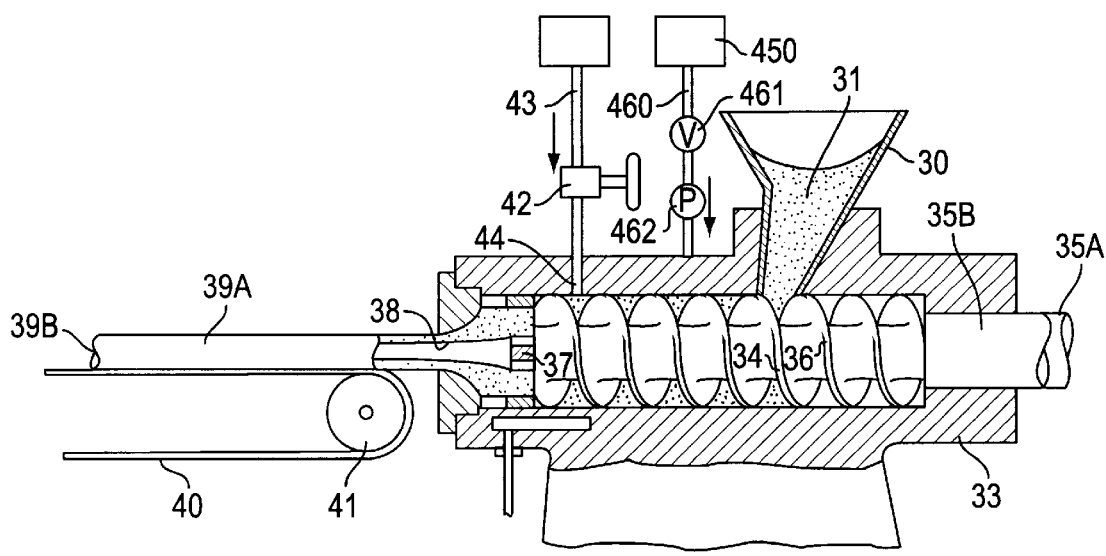
FIG. 4 is a cutaway side elevation view of extrusion apparatus used for extruding thermoplastic polymeric foamed tubing containing within the walls of the tubing fragrance for use in the sachets of our invention.

Similarly, an extruded tube which can be used as such or cut into smaller lengths is shown to be formed using the apparatus of FIG. 4. Thus, a single screw 35B taken alone or further together with a second screw 25A makes up part of an extruder in casing 33. Resin from resin funnel 30 is fed in at location 31 into the extrusion barrel upstream from the feeding of fragrance which is located at source 450. Simultaneously, fragrance from source 450 is fed through line 460 past valve 461 using pump 462 into the extrusion barrel. The extruder causes an intimate mixing of the fragrance with the resin in the screw conveyor threads 34 and 36. Simultaneously, upstream from the addition of the fragrance, gaseous blowing agent is fed through line 43 past valve 42 into the extrusion screws at location 44. The extruded tube is then forced through die 37 and orifice 38 onto conveyor belt 40 in the form of tube 39A which may be subsequently cut at location 39B. The conveyor belt is operated using roller 41.

The resulting extruded foam tubing or foamed pellets may be cut up for the purpose of creation of an article of manufacture which contains fragrance. Such article of manufacture may be molded using injection molding apparatus of the type set forth in FIGS. 5A, 5B and 6, or jet molding apparatus of the type set forth in FIG. 7.

Figure 5A:
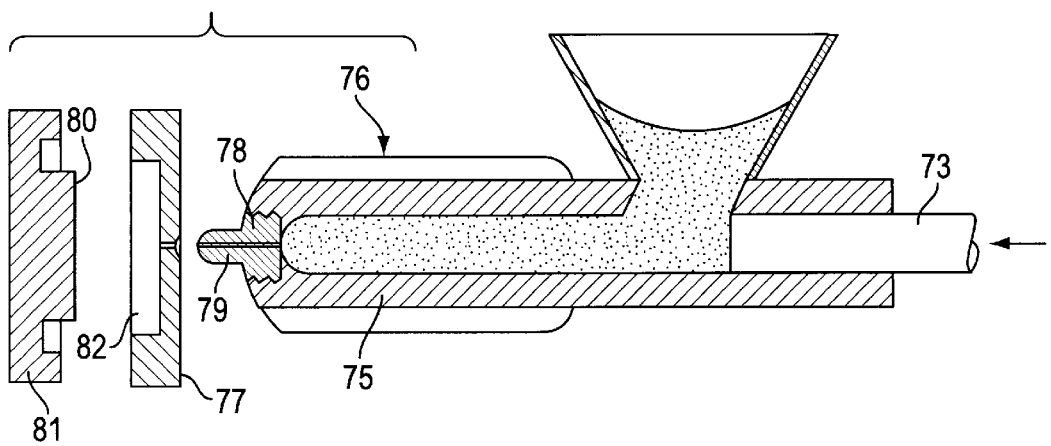
FIGS. 5A and 5B represent cutaway side elevation views of injection molding apparatus prior to and during the injection molding operation for the injection molding of fragrance-containing foamed polymeric pellets useful in practicing our invention.
Figure 5B:
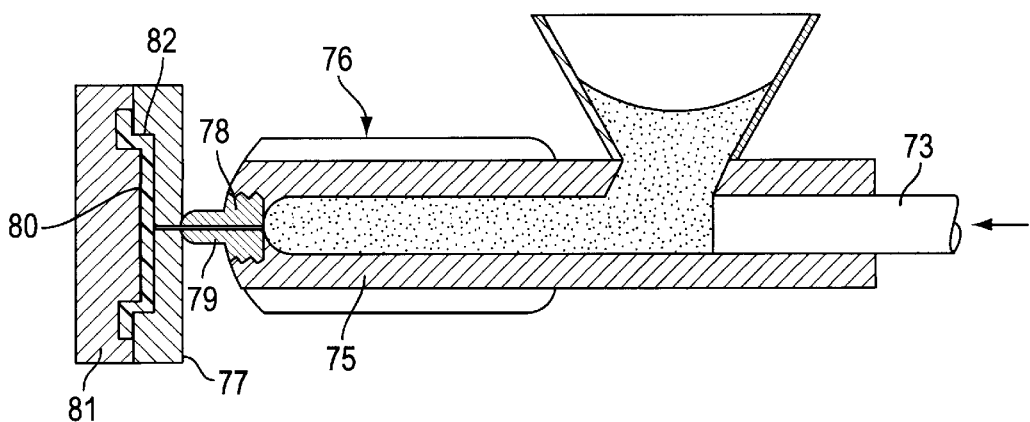

FIGS. 5A and 5B show the injection molding apparatus in operation. In FIG. 5A, plunger 73 pushes the foamed fragrance-containing polymeric particles through cylinder 75 heated by heating unit 76 through die 78 out of orifice 79 into the mold 77/82/80/81. The mold is composed of a male portion 80 and female portion 82. Thus, in summary, the injection molding is characterized by the fact that the molding mix is preheated in a plasticizing cylinder having a cylinder liner 109 (as shown in FIG. 6) to a temperature high enough for it to retain a quasi-liquid condition and is then forced by plunger 89 through the plunger cylinder into heating cylinder 91 (the temperature for which is measured using a thermocouple in thermocouple container 94), into a closed mold 108 which is cold enough to "freeze" the mixture to a solid sufficiently rigid for ejection. Molding mix containing the foamed polymeric particles 86 is fed in the plasticizing cylinder through hopper 85. When the mold opens, the cylinder plunger 89 moves back permitting material to drop into the cylinder. On the closing stroke, the mold members lock tightly together and the cylinder plunger moves forward forcing the newly delivered material from the hopper into the heating zone of the cylinder 90. This material, in turn, displaces a "shot" of molten material through the nozzle 93 in the mold cavity through orifice 111. The mold is cooled so that the shot hardens quickly. Conditions are controlled so that the molten plastic just has time to reach the outer most recesses of the mold cavity before flow ceases. When the mold is opened, the formed piece is loosened by knockout pins 99, 100, 101 and 102. The function of the spreader 90 is to spread the mix into thin films and facilitate uniform heating as it passes toward the nozzle 93.

Figure 7:
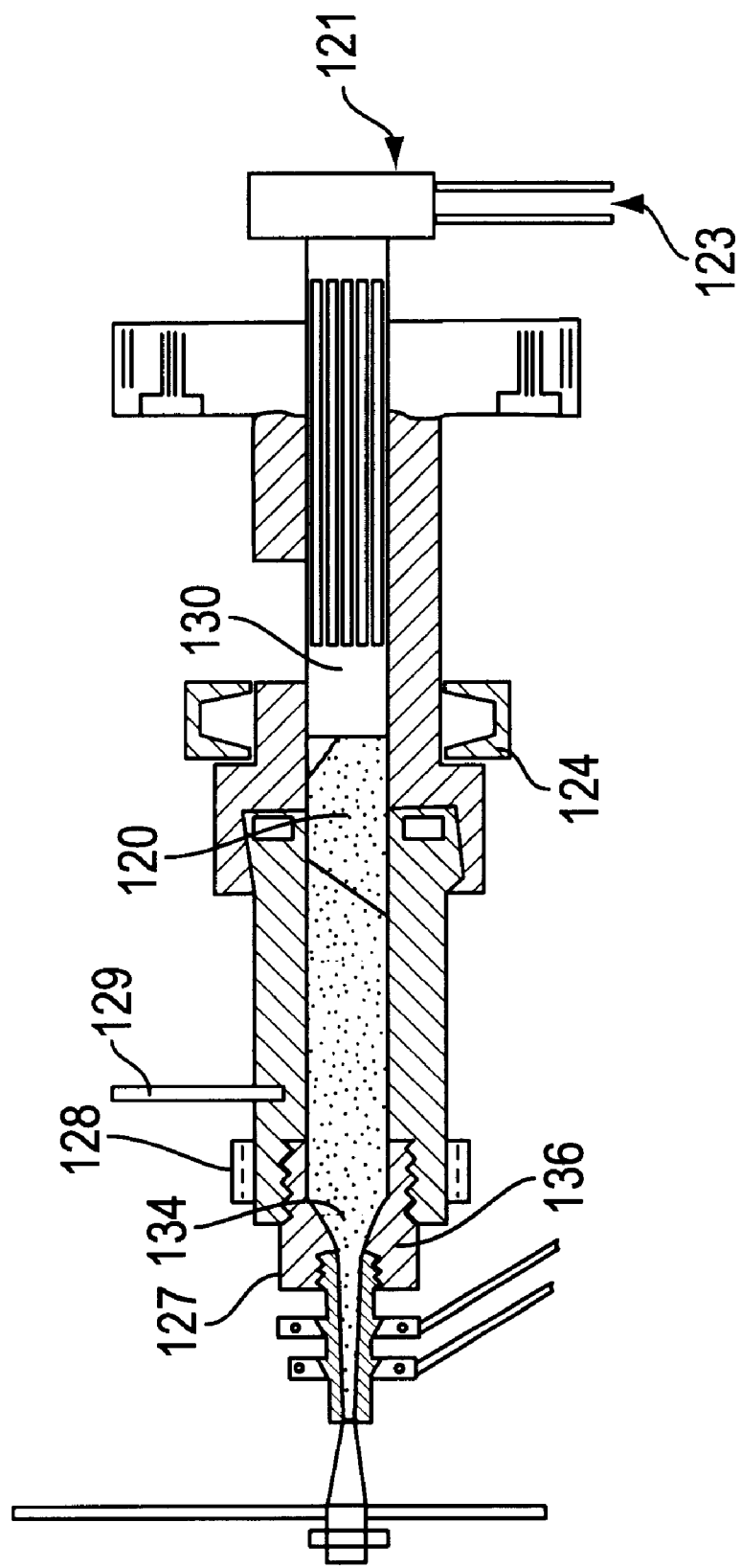
FIG. 7 is a cutaway side elevation schematic view of jet molding apparatus useful in forming articles of manufacture from the polymeric pellets containing fragrance.
Figure 8:
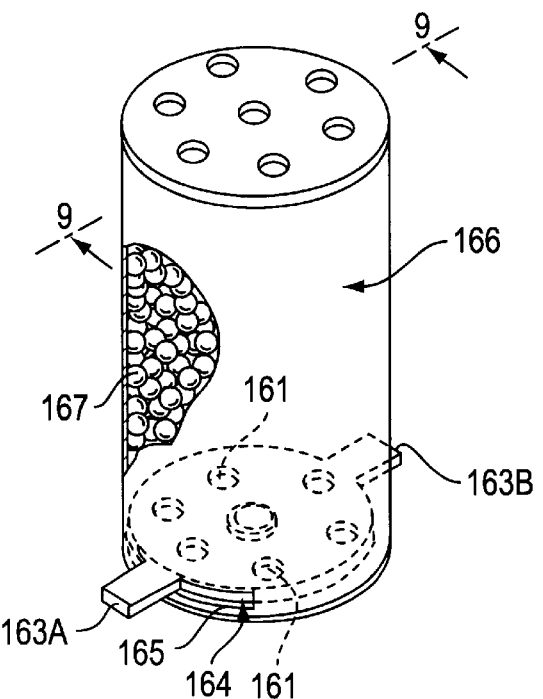
FIG. 8 is a partially cutaway perspective view of an article of manufacture useful as a sachet.
Figure 9:
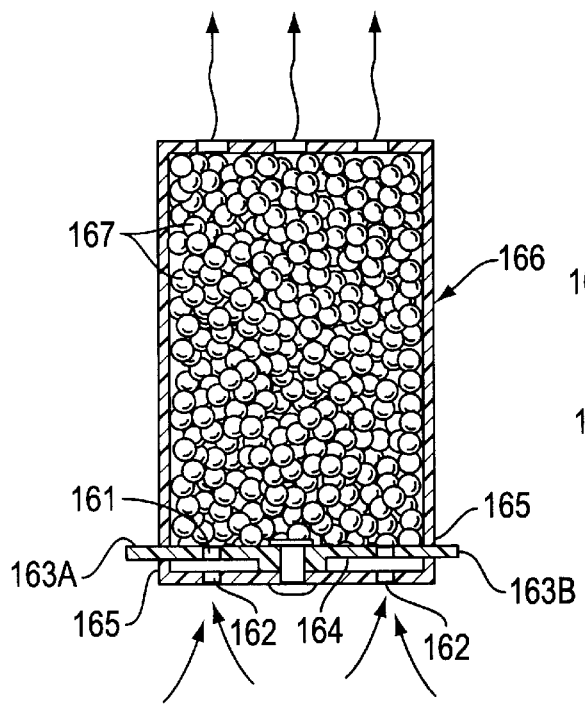
FIG. 9 is a cutaway side elevation view of the article of manufacture of FIG. 8 looking in the direction of the arrows.
Figure 10:
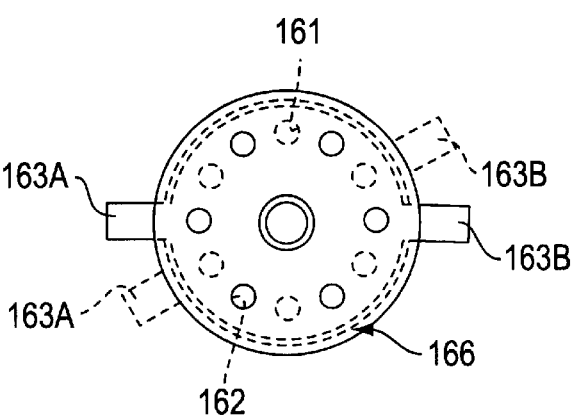
FIG. 10 is a top view of the article of manufacture of FIG. 8.

In FIG. 7, which is a schematic diagram of a cutaway elevation view of a jet molding apparatus useful in producing articles of manufacture using the foamed polymeric fragrance-containing particles of our invention, the mix 120 is fed into a hopper and from thence falls into a feed cylinder at 120 which is cooled using water cooling 124. The material is then moved forward toward the nozzle end of the cylinder consisting of a nozzle block containing a full taper 127 and heated by a band heater at 128. The amount of heat and rate of heating is measured using a controlling thermocouple 129. The pressure is supplied by the injection plunger 130 having water cooling connection 123 at location 121. As the mix nears the nozzle, mold heat is applied Temperatures of 150° F.–200° F. are maintained, and the mix is merely warmed in this zone. Under the high pressure of the injection plunger 130, the foamed polymeric fragrance-containing particles begin to flow into the nozzle 136 at location 134. Thus, for example, placed around the nozzle are two or more electrodes by means of which intense heat is generated by induction. The heat is transferred to the thin stream of mix as it passes through the nozzle 136. By this means, the temperature of the mix is raised almost instantaneously to 400° F.–500° F. Too high a jet molding temperature can create a destruction of the fragrance during the production of the fragrance-containing article of manufacture.

Figure 11:
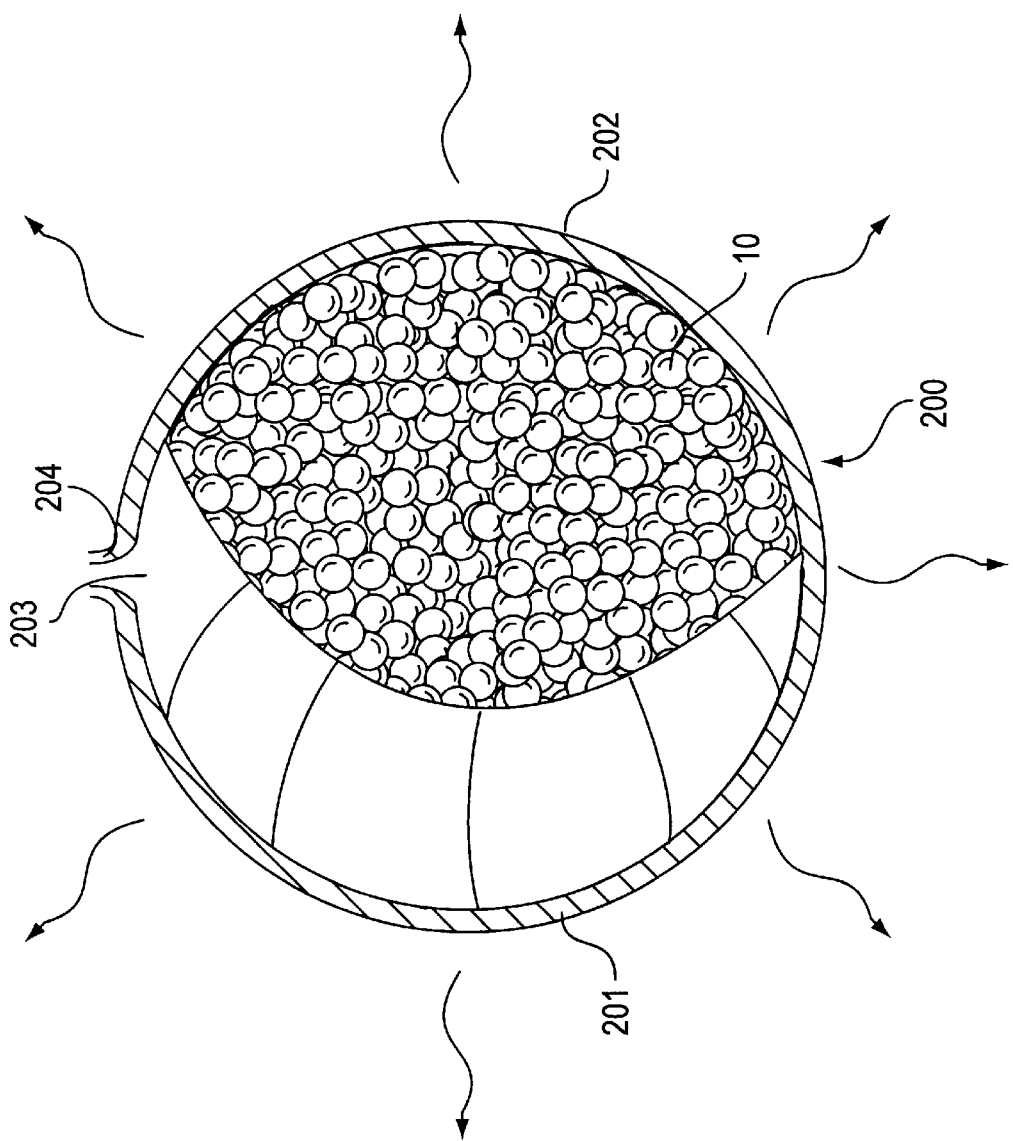
FIG. 11 is a cutaway perspective view of a sachet of our invention showing in schematic form the controllable release of fragrance through the walls of the sachet product.

The essence of our invention is a control release device made into a sachet using the various fragrances as listed in the table, supra. Such sachets are shown in FIGS. 8, 9, 10 and 11. Thus, after placing polymeric fragrance-containing pellets 167 into cylinder 166 (the pellets, for example, being pellets produced using the apparatus shown in FIGS. 2 and 3), the resulting article can be placed into a clothes closet or the like as hung from a hanger as indicated by reference numeral 204 in FIG. 11. As stated, supra, the sachet container is fabricated from porous, microporous or non-porous material indicated by reference numeral 201. The overall sachet of FIG. 11 is indicated by reference numeral 200. The fragrance-containing polymeric pellets are indicated by reference numeral 10. The surface through which the fragrance is transmitted on storage is indicated by reference numeral 202.

Figure 12B:
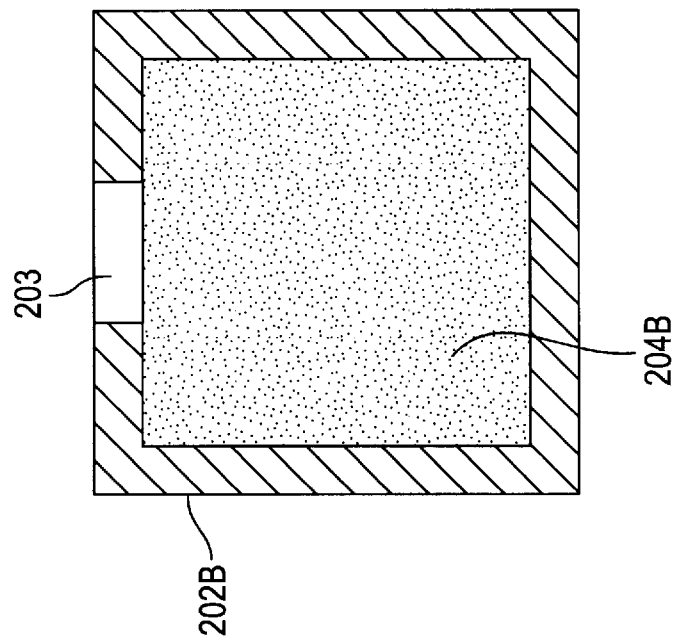
FIGS. 12A and 12B show prefabrication portions of the sachet of FIG. 11.
Figure 12A:
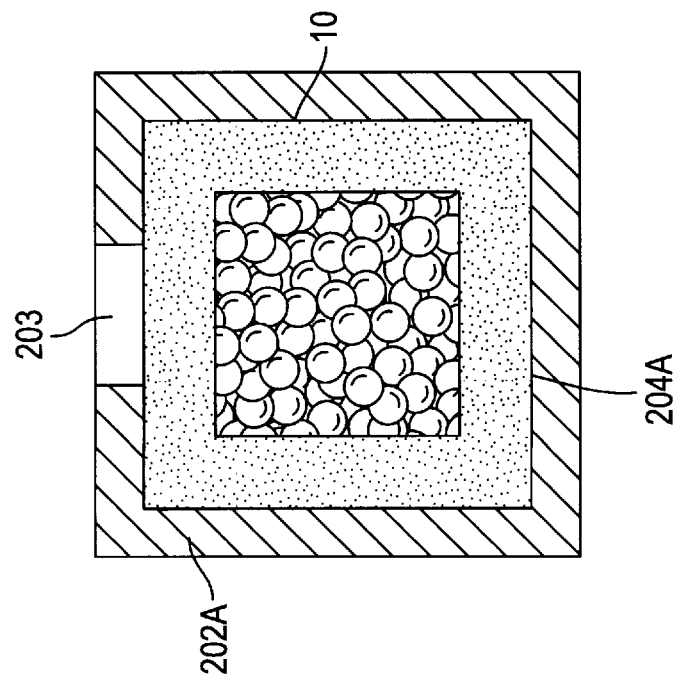

In fabricating the sachets of our invention, two square prefabricated portions of the outer container are shown in FIGS. 12A and 12B to have heat-sealable edges 202A and 202B. Microporous polymer particles as produced using the apparatus of FIGS. 2 and 3 are placed on the surface of the prefabricated section as indicated by reference numeral 10, the surfaces of the prefabricated sections being indicated by reference numerals 204A and 204B.

Referring to FIGS. 16 and 17, the apparatus used in producing polymeric fragrances useful in the practice of cur invention comprises a device for forming scented polyolefin (for example) pellets, which comprises a vat or container 1212 into which a mixture of polyolefin such as polyethylene and an aromatic substance or scented material is placed (in this case at least one of the fragrances useful in the practice of our invention).

The container is closed by an air-tight lid 1228 and the air-tight lid 1228 is clamped to the container 1212 by bolts 1265.

A stirrer 1273 traverses the lid or cover 1228 in an air-tight manner and is rotated in a suitable manner.

Container 1212 having heating coils 1212A which are supplied with electric current through cable 1224 from a rheostat or control 1216 is operated to maintain a temperature inside the container 1212 such that polyethylene or other thermoplastic polymer in the container will be maintained in the molten or liquid state. It has been found advantageous to employ a colorless, odorless polymer (e.g., polyethylene) with viscosity ranging between 180 and 220 Saybolt seconds and having a melting point in the range of 200°–280° F. The heater 1212A is operated to maintain the upper portion of the container 1212 within a temperature range of from 250°–350° F. The bottom portion of the container is heated by means of heating coils 1212A heated through control 1220 connected thereto through a connecting wire 1222 to maintain the lower portion of the container within a temperature range of from 250°–350° F.

Thus, polymer (e.g., polyethylene) is added to container 1212 and is heated from 10–12 hours whereafter a scented aroma imparting material (at least one of the fragrances useful in the practice of our invention) is added quickly to the melt. The material must be compatible with the polyolefin and forms a homogeneous liquid melt therewith. The scented material is of a type for the particular aroma desired and formulated specifically for the scenting purpose for which the polyolefin will be employed.

Generally, about 5–30% by weight of the scented material (containing at least one of the fragrances useful in the practice of our invention) are added to the polyolefin.

After the scent imparting material (e.g., a composition containing at least one of the fragrances useful in the practice of our invention) is added to the container 1212, the mixture is stirred for a few minutes, for example, 5–15 minutes and maintained within the temperature range as indicated, supra, by means of heating coils 1212A.

The controls 1216 and 1220 are connected, respectively, through cables 1214 and 1222, respectively, to heating coils 1212A. The said controls 1216 and 1220 are also connected through cables 1224 and 1226, respectively, to a suitable power supply of electric current for supplying the electric power to the heating coils 1212A for heating purposes.

Thereafter, the valve "V" is opened permitting the mass to flow outwardly through conduit 1218/1232 having a multiplicity of orifices 1234, adjacent to the lower side thereof. The outer end of the conduit 1218/1232 is closed so that the liquid polymer (e.g., polyolefin) and aroma imparting material (e.g., at least one of the fragrances useful in the practice of our invention) will continuously drop through orifices 1234 downwardly from conduit 1232. During this time, the temperature of the polymer (e.g., polyolefin) and scent imparting material (e.g., a mixture containing at least one of the fragrances useful in the practice of our invention) is accurately controlled so that a temperature in the range of from about 210°–275° F. will exist in the conduit 1218/1232. The regulation of the temperature through controls 1216 and 1220 is essential in order to insure temperature balance to provide for the continuous dropping or dripping of molten polymer (e.g., polyethylene) and scenting material (e.g., one or more of the fragrances useful in the practice of our invention) mixture through the orifices 1234 at a rate which will insure the formation of droplets 1236 which will fall downwardly onto a moving conveyor belt 1238 caused to run between conveyor wheels 1240 and 1242 beneath the conduit 1232.

When the droplets 1236 fall onto the conveyor belt 1238, they form pellets 1244 which harden almost instantaneously and fall off the end of the conveyor belt 1238 into a container 1245 and utilized in processes as illustrated, infra.

A feature of this aspect of the process of our invention is the provision for moistening the conveyor belt 1238 to insure rapid formation of the solid polymeric (e.g., polyolefin) scented pellets 1244 without sticking to the belt. The conveyor belt 1238 is advantageously fabricated of a material which will not normally stick to a melted plastic, but a moistening means 1248 insures a sufficiently cold temperature of the belt surface for an adequate formation of the pellets 1244. The adequate moistening means comprises a container 1250 which is continuously fed with water 1254 to maintain a level for moistening a sponge element 1256 which bears against the exterior of the conveyor belt 1238.

Figure 13A:
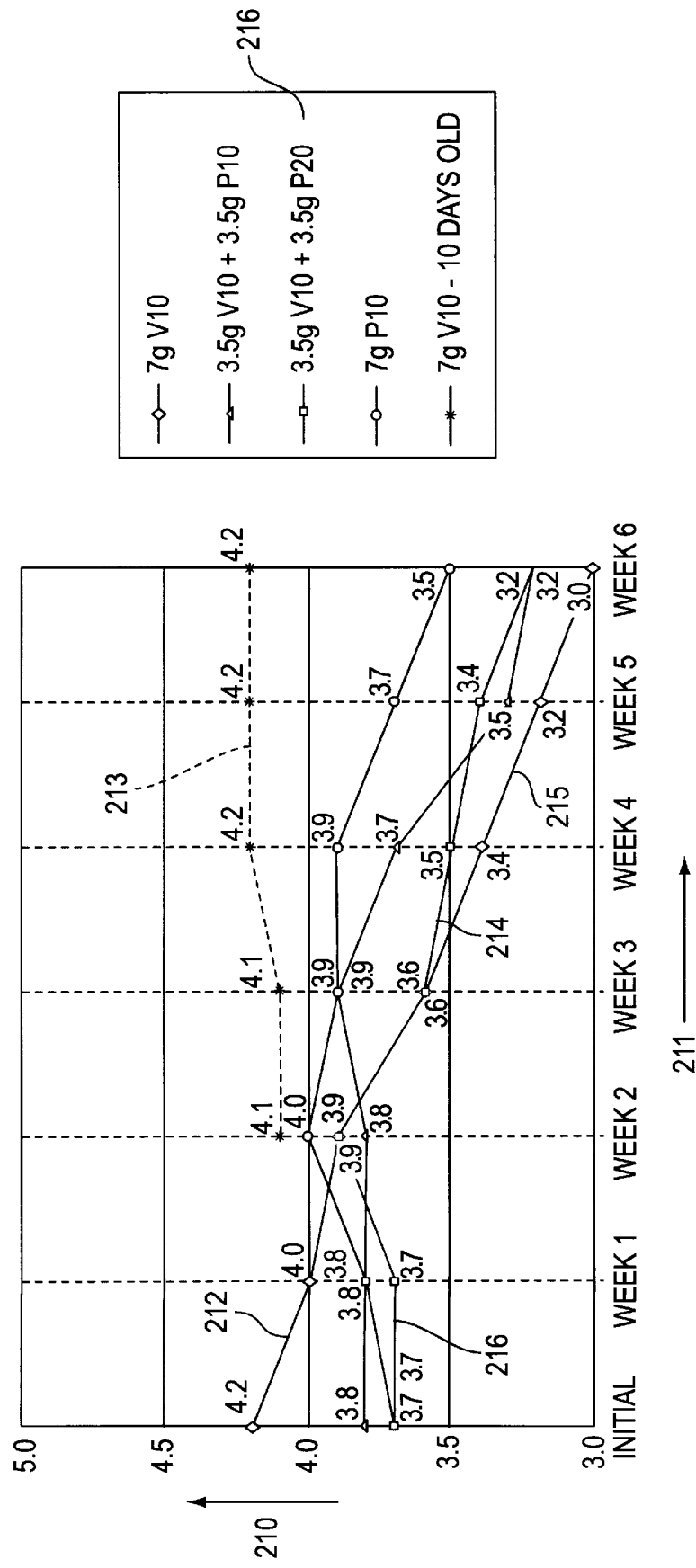
FIG. 13A sets forth a comparison of in-use products of FIG. 13, showing for each product strength on a scale of zero to 5 versus time.
Figure 14B:
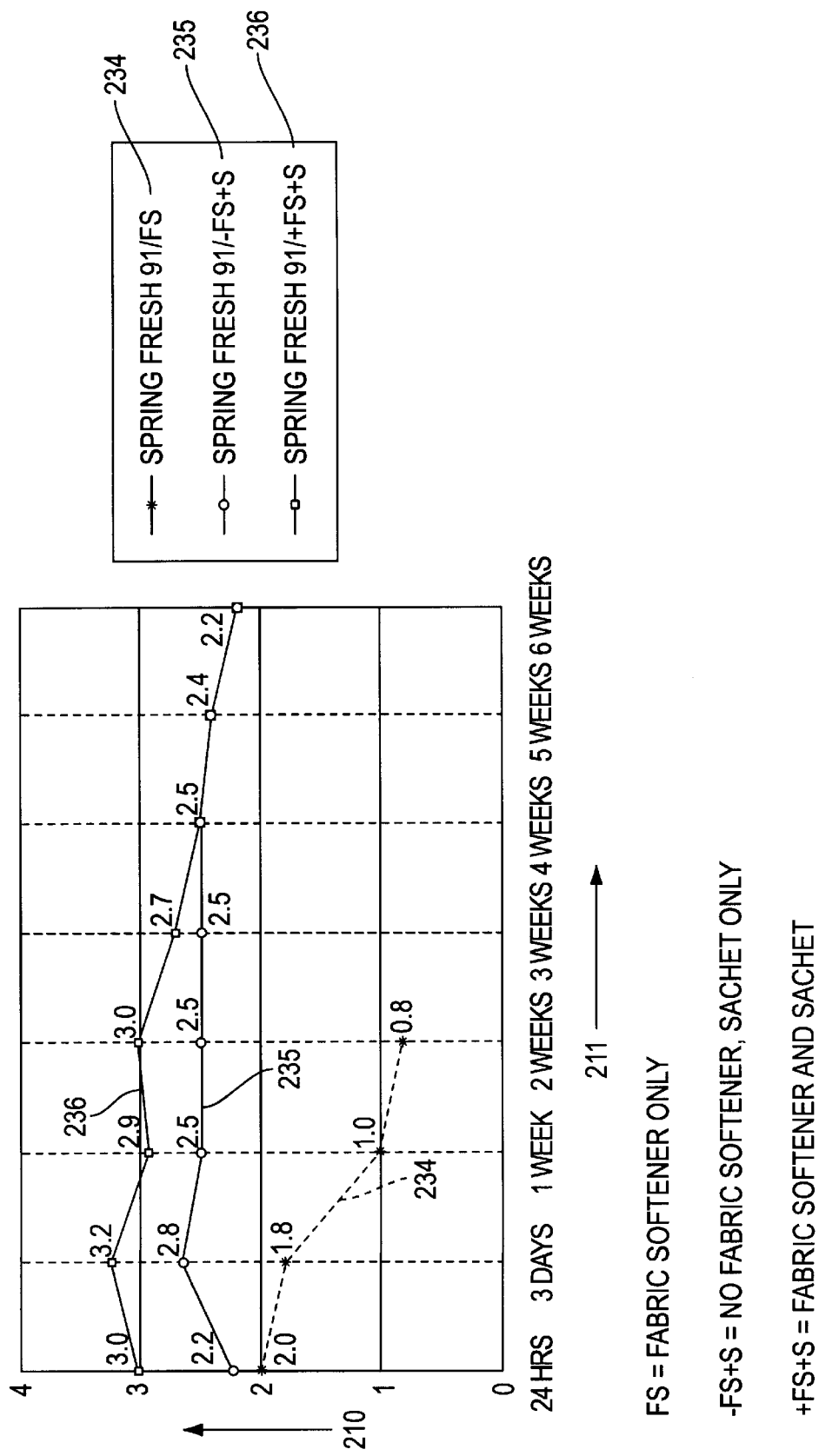

Referring to FIG. 13A, the strength on a scale of 0 to 5 is shown on the Y axis using reference numeral 210 and time in weeks is shown on the X axis using reference numeral 211. The graph indicted by reference numeral 213 is the graph for 7 grams of vermiculite, 10 days old and containing 10% by weight of fragrance. The graph indicated by reference numeral 212 is the graph for 7 grams of vermiculite containing 10% fragrance. The graph indicated by reference numeral 214 is the graph for a mixture of 3.5 grams of vermiculite containing 10% fragrance and 3.5 grams of extruded polymeric particles containing 20% fragrance. Graph 214, in the initial one week phase is indicated using reference numeral 216. Graph 212, in the final phase is indicated using reference numeral 215.

Figure 13B:
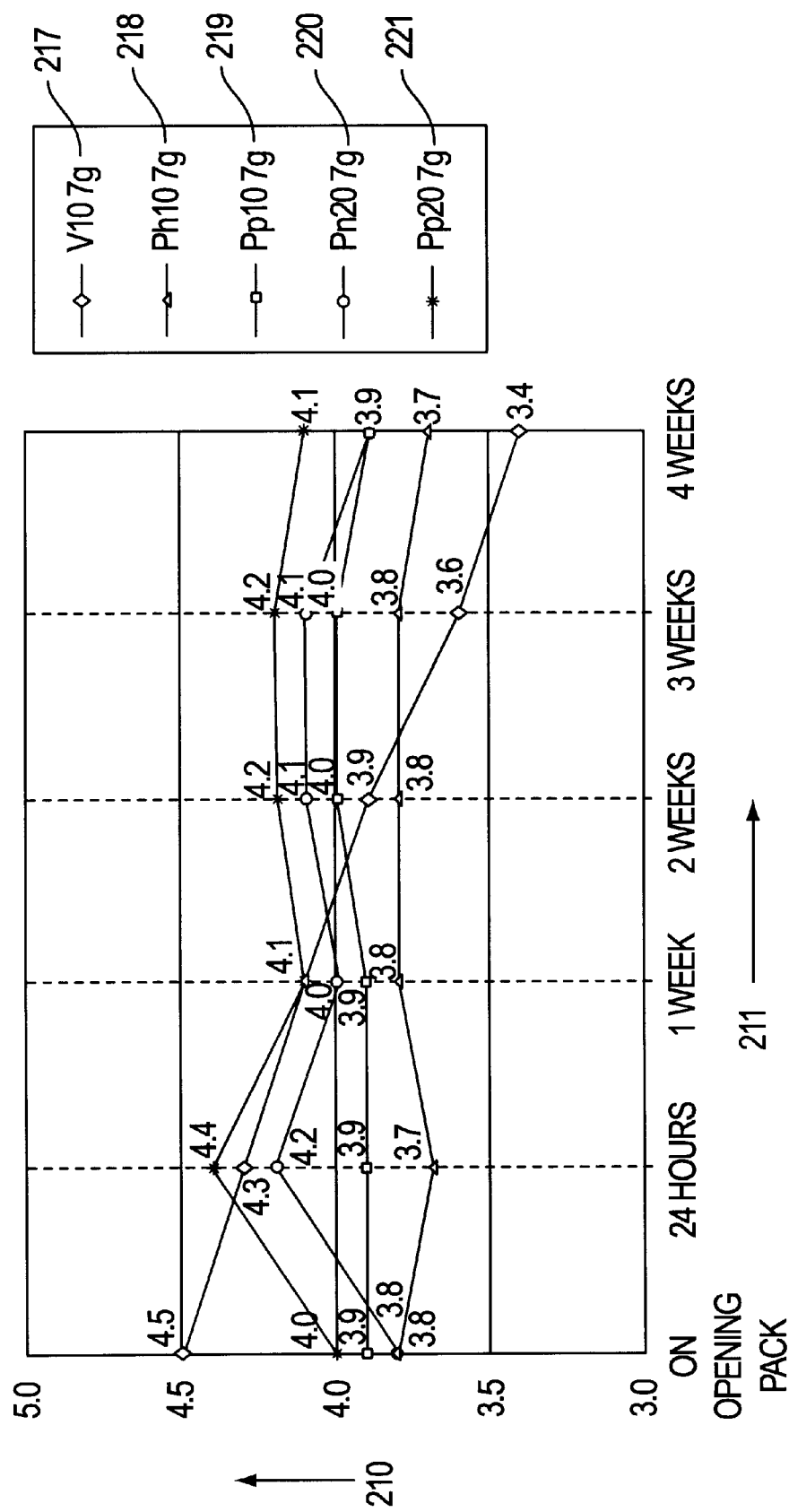

In FIG. 13B, the graph indicated by reference numeral 217 is for 7 grams of vermiculite containing 10% fragrance. The graphs indicated by reference numerals, 218, 219, 220 and 221 are for 7 grams of perfumed polymer with the graphs indicated by reference numerals 218 and 219 being for perfumed polymer containing 10% fragrance, and the graphs indicated by reference numerals 220 and 221 being for perfumed polymer containing 20% fragrance.

In FIG. 13C, the graph indicated by reference numeral 222 is the graph for the use in a sachet of 7 grams of vermiculite containing 10% fragrance. The graphs indicated by reference numerals 223, 224, 225 and 226 are for perfumed polymer pellets in an amount of 14 grams contained in the sachet. The pellets shown in graphs 223 and 224 contain 10% by weight fragrance, and the pellets shown in graphs 225 and 226 contain 20% by weight fragrance.

Figure 13D:
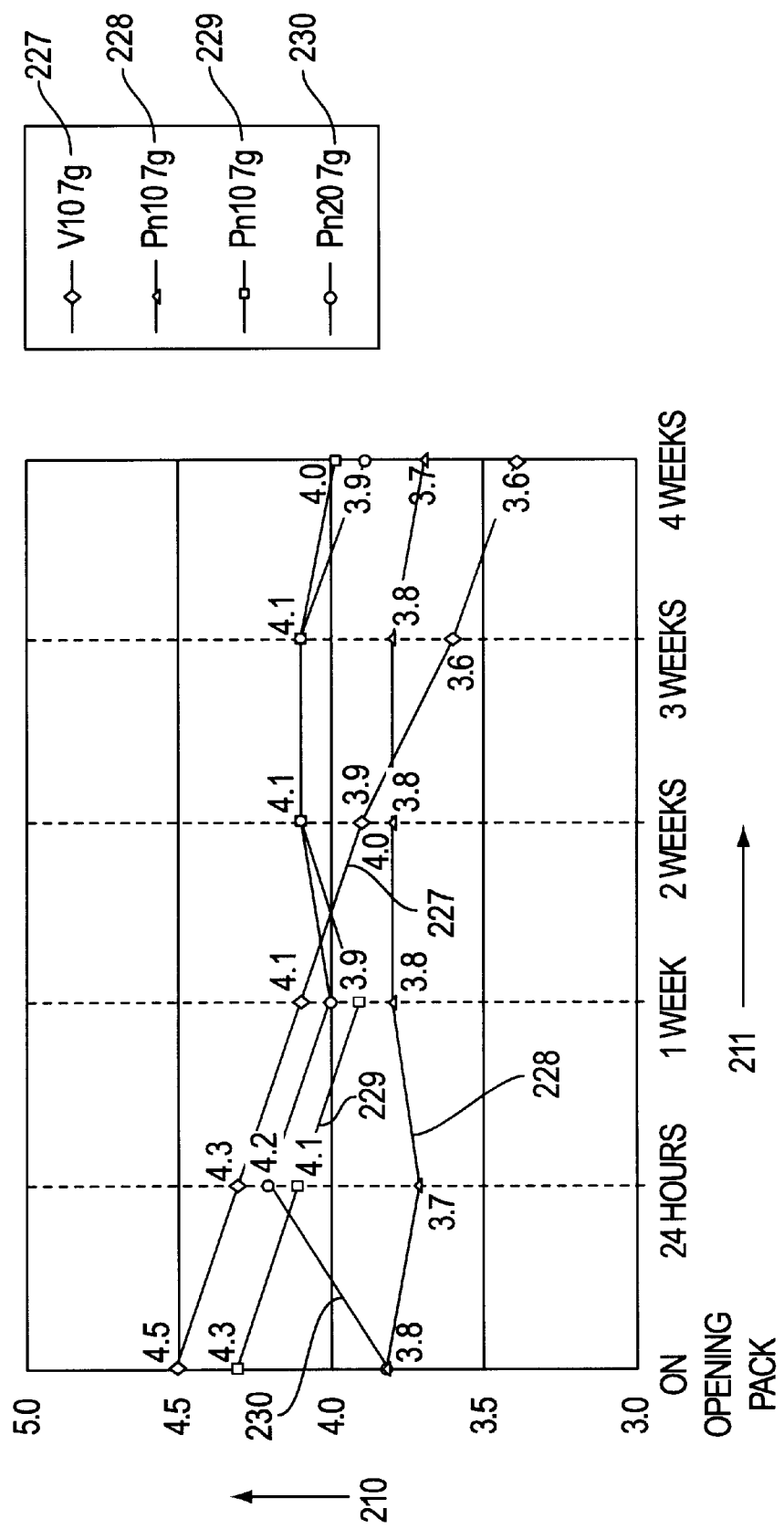

Referring to FIG. 13D, the graph indicated by reference numeral 227 is for a sachet containing merely 7 grams of vermiculite containing 10% by weight fragrance. The graph indicated by reference numeral 228 is for perfumed polymer pellets (7 grams) containing 10% by weight finance. The graph indicated by reference numeral 229 is for perfumed polymer pellets containing 10% by weight perfume with the total amount of pellets being 7 grams. The graph indicated by reference numeral 230 is for 7 grams of perfumed polymer pellets containing 20% by weight perfume.

Figure 14D:
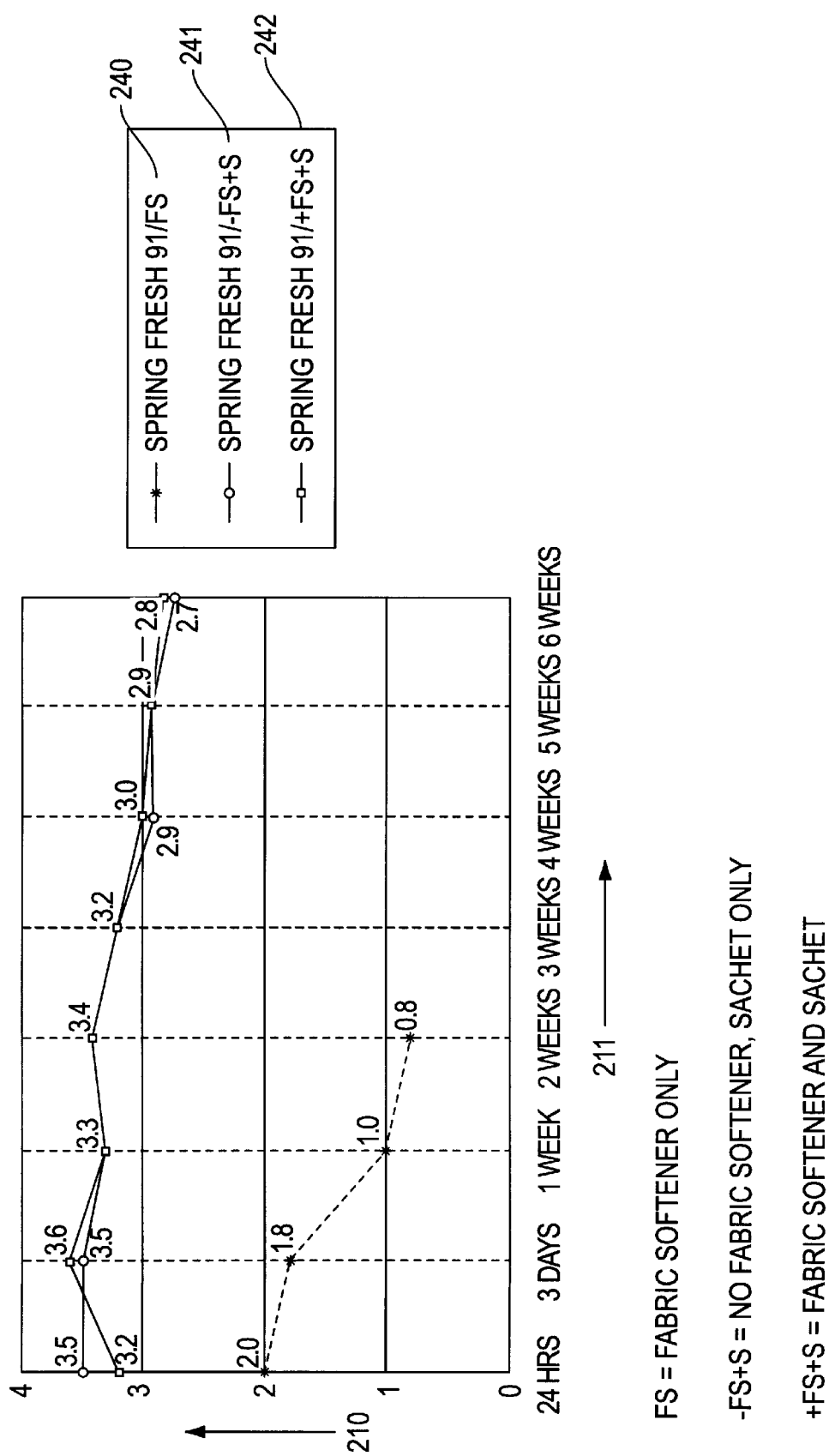

In FIGS. 14A, 14B, 14C, 14D and 14F, intensity of perfume is set forth on a scale of 0 to 4 (as defined in FIG. 14). In FIG. 14A, the graph indicated by reference numeral 231 is for a given fragrance used in a sachet in conjunction with fabric softeners. The graph indicated by reference numeral 231 is for the use of a "morning fresh" fabric softener only. The graph indicated by reference numeral 232 is for the use of a sachet containing polymeric pellets, but no fabric softener. The graph indicated by reference numeral 233 is for use of both fabric softener and sachet using the "morning fresh" fragrance.

In FIG. 14B, the graph indicated by reference numeral 234 shows what happens when fabric softener only is used, but no sachet of our invention. The graph indicated by reference numeral 235 is for the use of the sachet only, using "spring fresh" fragrance. The graph indicated by reference numeral 236 is for the combination of fabric softener and sachet, using "spring fresh" fragrance.

Referring to FIG. 14C, the graph indicated by reference numeral 237 shows the use of "morning fresh" with fabric softener only, but no sachet. The graph indicated by reference numeral 238 is for the use of a sachet only containing polymeric pellets, but no fabric softener. The graph indicated by reference numeral 239 is for the use of both the sachet containing polymeric pellets containing "morning fresh" fragrance and the fabric softener.

Referring to FIG. 14D, the graph indicated by reference numeral 240 is the graph for the use of "spring fresh" fragrance with fabric softener only. The graph indicated by reference numeral 241 is the graph for the use of "spring fresh" fragrance with fabric softener and in polymeric particles located in the sachet. The graph indicated by reference numeral 242 is for the use of the combination of fabric softener with "spring fresh" fragrance in the polymeric pellets in the sachet of our invention.

Referring to FIG. 14E, the graph indicated by reference numeral 243 is the graph for the use of 7 grams of polymeric pellets containing 10% fragrance. The graph indicated by reference numeral 244 is for the use in the sachet of our invention of 7 grams of polymeric pellets containing 20% fragrance. The graph indicated by reference numeral 245 is for the use of 14 grams of polymeric pellets containing 10% fragrance. The graph indicated by reference numeral 246 is for the use of 14 grams of polymeric pellets in the sachet containing 20% by weight of fragrance.

What is claimed is:

1. A three-dimensional sachet article located in a three-dimensional space comprising:

(1) non-rigid, hollow containment means consisting of a non-rigid, non-perforated container wall, which is a continuous, thin lamina separating an inner void from an outer environment, totally surrounding said inner void; having a height of from about 3 inches up to about 6 inches and a width of from about 2 inches up to about 5 inches; and having a measurement of weave of from about 10 up to about 120 grams per square centimeter, and which is porous to perfumes having a calculated $\log_{10}P$ of from about 3 up to about 8; and (ii) contained within a major proportion of said inner void and supported by said non-perforated container wall, a plurality of extruded polymeric perfume-containing and evolving particles having a total weight of from about 2 grams up to about 14 grams and a diameter of from about 3 mm up to about 7 mm, each of which contains within the interstices, thereof from about 5 up to about 45% by weight of a perfume composition having a calculated $\log_{10}P$ of from about 3 up to about 8, and a boiling point at atmospheric pressure of greater than 250° C., which perfume composition is emitted in a controllably releasable manner over an extended period of time into said inner void and then into said outer environment.

2. The article of claim 1 wherein addition to the plurality of extruded polymeric perfume-containing and evolving particles contained within said inner void, there is also contained in said inner void in admixture with said extruded particles, particles of vermiculite.

3. A process for fragrancing a third-dimensional space over an extended period of time comprising the step of placing the sachet article of claim 1 within said three-dimensional space.

4. A process for fragrancing a three-dimensional space over an extended period of time comprising the step of placing the sachet article of claim 2 within said three-dimensional space.

5. A process for forming the article of claim 1 comprising the steps of:

(i) providing a first planar, non-rigid lamina consisting of a polymer porous to perfumes having a calculated $\log_{10}P$ of from about 3 up to about 8 and having a circumference which is heat sealable over substantially its entire distance;

(ii) placing on said first planar lamina a plurality of extruded polymeric particles, each of which contains within the interstices thereof from about 5 up to about 45% by weight of a peruse composition having a calculated $\log_{10}P$ of from about 3 up to about 8, which particles emit said perfume composition in a controllably releasable manner over an extended period of time;

(iii) providing a second planar lamina having a geometry substantially identical to said first planar lamina consisting of a polymer porous to perfumes having a calculated $\log_{10}P$ of from about 3 up to about 8 and having a circumference which is heat sealable substantial over its entire length;

(iv) placing said second planar lamina in contact with said first planar lamina so that their respective circumferences are juxtaposed with one another; and (v) applying sufficient heat to an area proximate said entire circumferences, whereby said first planar lamina is sealed to said second planar lamina along the entire circumferences of said first planar lamina and said second planar lamina.

6. The article of claim 1 wherein the extruded, polymeric, perfume-containing and evolving particles are polymeric foam particles.

7. The article of claim 2 wherein the extruded, polymeric, perfume-containing and evolving particles are polymeric foam particles.

* * * * *